United States Patent [19]
Forstrom et al.

[11] Patent Number: 5,986,049
[45] Date of Patent: Nov. 16, 1999

[54] PURIFIED THROMBOPOIETIN AND METHOD OF MAKING IT

[75] Inventors: John W. Forstrom, Seattle; Catherine E. Lofton-Day, Brier; Si Lok, Seattle, all of Wash.

[73] Assignee: ZymoGenetics, Inc., Seattle, Wash.

[21] Appl. No.: 08/457,254

[22] Filed: Jun. 1, 1995

Related U.S. Application Data

[63] Continuation of application No. 08/366,859, Dec. 30, 1994.

[51] Int. Cl.⁶ .............................. A61K 38/00; C07K 1/00
[52] U.S. Cl. .............................................. 530/344; 514/12
[58] Field of Search ................................ 514/12; 530/399

[56] References Cited

U.S. PATENT DOCUMENTS 5,541,085  7/1996  Holly et al. ............................. 435/69.1

FOREIGN PATENT DOCUMENTS

91/18925  12/1991  WIPO ...................................... 514/12

OTHER PUBLICATIONS

Lok et al., *Nature 369*: 565–568, 1994.
Bartley et al;. *Cell 77*: 1117–1124, 1994.
McDonald, *Am. J. Ped. Hematol./Oncol. 14*: 8–21, 1992.
McDonald, *Exp. Hemtol. 16:*201–205, 1988.
de Sauvage et al., *Nature 369:* 533–538, 1994.
Li et al., *Blood 84 (10 Suppl. 1)*, 330a, abstr. No. 1307.
Osborn et al., *Protein Science 3 (Suppl. 1)*, 140 abstr. No. 504–M.
McDonald et al., *Database Biosis (abstract)*: Acc. nr. 87: 376706; BA84; 63203, 1987.
McDonald et al., *Database Biosis (abstract)*: Acc. nr. 85: 421631; BA80:91623, 1985.
Kaushansky, *Stem Cells 12*: 91–97, 1994.
Metcalf, *Nature 369*: 519–520, 1994.
Scopes, *Protein Purification: Principles and Practice 2nd ed.*: Ch. 5, 1987.
McDonald et al., *Blood 85*: 292–294, 1995.

*Primary Examiner*—Avis M. Davenport
*Attorney, Agent, or Firm*—Gary E. Parker

[57] ABSTRACT

Purified mammalian thrombopoietin proteins and methods of making them are disclosed. The proteins are characterized by a $M_r=70,000\pm10,000$ daltons as determined by SDS-polyacrylamide gel electrophoresis under denaturing conditions and are at least 90% pure with respect to contaminating proteins. The proteins can be prepared by a method in which thrombopoietin is adsorbed to and eluted from a polypeptide comprising a ligand-binding domain of an MPL receptor, then the eluted thrombopoietin is fractionated by anion exchange chromatography.

10 Claims, 2 Drawing Sheets

PURIFIED THROMBOPOIETIN AND METHOD OF MAKING IT

This is a continuation application of co-pending application Ser. No. 08/366,859, filed Dec. 30, 1994.

BACKGROUND OF THE INVENTION

Hematopoiesis is the process by which blood cells develop and differentiate from pluripotent stem cells in the bone marrow. This process involves a complex interplay of polypeptide growth factors (cytokines) acting via membrane-bound receptors on the target cells. cytokine action results in cellular proliferation and differentiation, with response to a particular cytokine often being lineage-specific and/or stage-specific. Development of a single cell type, such as a platelet, from a stem cell may require the coordinated action of a plurality of cytokines acting in the proper sequence.

The known cytokines include the interleukins, such as IL-1, IL-2, IL-3, IL-6, IL-8, etc.; and the colony stimulating factors, such as G-CSF, M-CSF, GM-CSF, erythropoietin (EPO), etc. In general, the interleukins act as mediators of immune and inflammatory responses. The colony stimulating factors stimulate the proliferation of marrow-derived cells, activate mature leukocytes, and otherwise form an integral part of the host's response to inflammatory, infectious, and immunologic challenges.

Various cytokines have been developed as therapeutic agents. For example, erythropoietin, which stimulates the development of erythrocytes, is used in the treatment of anemia arising from renal failure. Several of the colony stimulating factors have been used in conjunction with cancer chemotherapy to speed the recovery of patients' immune systems. Interleukin-2, α-interferon and γ-interferon are used in the treatment of certain cancers.

An activity that stimulates megakaryocytopoiesis and thrombocytopoiesis has been identified in body fluids of thrombocytopenic animals and is referred to in the literature as "thrombopoietin" (recently reviewed by McDonald, *Exp. Hematol.* 16:201–205, 1988 and McDonald, *Am. J. Ped. Hematol. Oncol.* 14:8–21, 1992).

Recently, several groups have identified and/or cloned a protein that binds to the cellular MPL receptor and stimulates megakaryocytopoiesis and thrombocytopoiesis. See, de Sauvage et al., *Nature* 369:533–538, 1994; Lok et al., *Nature* 369:565–568, 1994; Kaushansky et al., *Nature* 369:568–571, 1994; Wendling et al., *Nature* 369:571–574, 1994; and Bartley et al., *Cell* 77:1117–1124, 1994. It has been proposed that this protein be termed thrombopoietin (Kaushansky et al., ibid.). Although this protein has been shown to stimulate platelet production in vivo (Kaushansky et al., ibid.), it appears to be subject to proteolysis and was isolated in heterogeneous or degraded form (Bartley et al., ibid.; de Sauvage et al., ibid.).

Proteolysis and heterogeneity are significant problems that can impede the development of new pharmaceutical agents. There remains a need in the art for homogeneous, undegraded preparations of thrombopoietin and for methods of making such preparations. The present invention fulfills these needs and provides other, related advantages.

SUMMARY OF THE INVENTION

It is an object of the present invention to provide purified preparations of thrombopoietin, including human thrombopoietin.

It is a further object of the invention to provide homogeneous preparations of thrombopoietin.

It is an additional object of the invention to provide methods for purifying and fractionating thrombopoietin.

Within one aspect, the present invention provides, purified mammalian thrombopoietin (TPO) characterized by an $M_r=70,000\pm10,000$ daltons as determined by SDS-polyacrylamide gel electrophoresis under denaturing conditions, which is at least 90% pure with respect to contaminating proteins as determined by SDS-polyacrylamide gel electrophoresis and silver staining. Within one embodiment, the purified TPO is essentially free of TPO species of $M_r<55$ kD. Within other embodiments, the purified TPO is mouse TPO, primate TPO or human TPO.

Within another aspect, the present invention provides a method for purifying thrombopoietin from a biological fluid comprising (a) applying a biological fluid containing thrombopoietin to a polypeptide comprising a ligand-binding domain of an MPL receptor, which polypeptide is bound to a solid support, whereby the thrombopoietin is adsorbed to the polypeptide; (b) washing the polypeptide to elute unadsorbed material; (c) eluting the adsorbed thrombopoietin from the polypeptide; (d) fractionating the eluted thrombopoietin by anion exchange chromatography; and (e) collecting the fractionated thrombopoietin. Within one embodiment, the biological fluid is conditioned cell culture media or milk. Within another embodiment, the biological fluid is concentrated, conditioned cell culture media. Within yet another embodiment, the method further comprises the step of concentrating the biological fluid before applying it to the receptor polypeptide. Within another embodiment, the polypeptide comprises a ligand-binding domain of a mouse or human MPL receptor. Within an additional embodiment, the polypeptide consists essentially of residues 27–480 of SEQ ID NO:7.

Within an additional aspect of the invention, TPO is purified by the methods disclosed above, and the collected TPO is characterized by an $M_r=70,000\pm10,000$ daltons as determined by SDS-polyacrylamide gel electrophoresis under denaturing conditions and is at least 90% pure with respect to contaminating proteins as determined by SDS-polyacrylamide gel electrophoresis and silver staining. Within one embodiment, the collected thrombopoietin is essentially free of TPO species of $M_r<55$ kD.

These and other aspects of the invention will become evident upon reference to the following detailed description and the attached drawings.

DETAILED DESCRIPTION OF THE INVENTION

Figure 1:
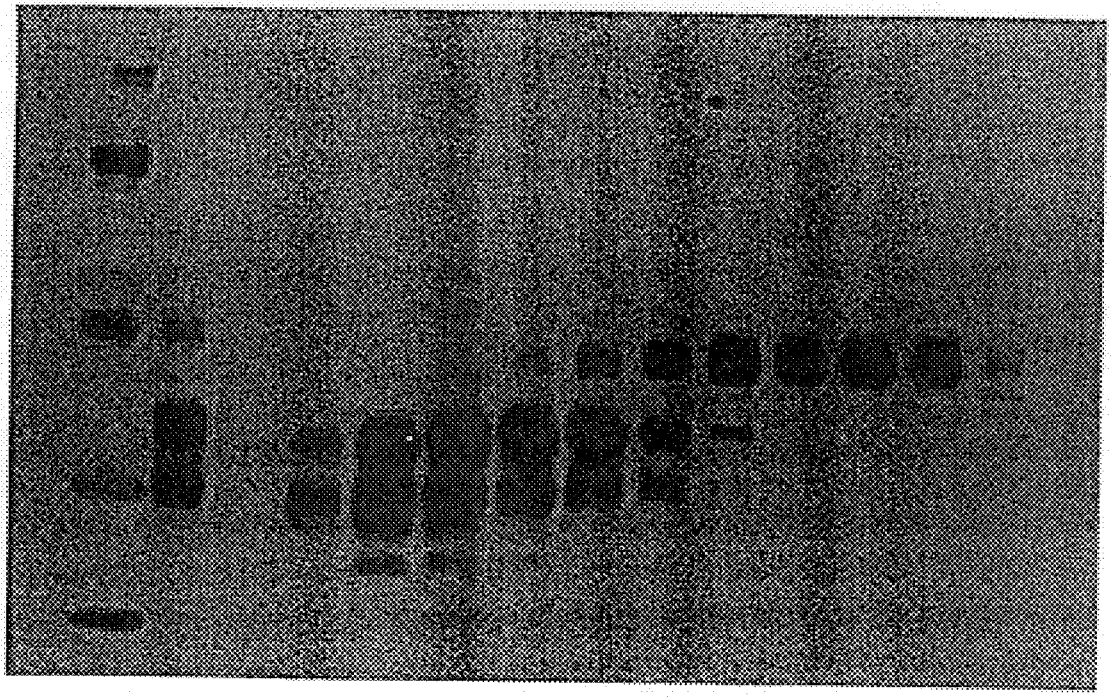
FIG. 1 illustrates the separation of $M_r\cong70$ kD and lower molecular weight forms of mouse TPO. The leftmost two lanes are molecular weight markers and unfractionated TPO.

Prior to describing the present invention in detail, it may be helpful to define certain terms used herein:

Allelic variant: An alternative form of a gene that arises through mutation, or an altered polypeptide encoded by the mutated gene. Gene mutations can be silent (no change in the encoded polypeptide) or may encode polypeptides having altered amino acid sequence.

Biological fluid: Any fluid derived from or containing cells, cell components or cell products. Biological fluids include, but are not limited to, cell culture supernatants, cell lysates, cleared cell lysates, cell extracts, tissue extracts, blood, plasma, serum, milk and fractions thereof.

cDNA: Complementary DNA, prepared by reverse transcription of a messenger RNA template, or a clone or amplified copy of such a molecule. Complementary DNA can be single-stranded or double-stranded.

Expression vector: A DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both. The term "operably linked" indicates that the segments are arranged so that they function in concert for their intended purposes, e.g. transcription initiates in the promoter and proceeds through the coding segment to the terminator.

Gene: A segment of chromosomal DNA that encodes a polypeptide chain. A gene includes one or more regions encoding amino acids, which in some cases are interspersed with non-coding "intervening sequences" ("introns"), together with flanking, non-coding regions which provide for transcription of the coding sequence.

Promoter: The portion of a gene at which RNA polymerase binds and mRNA synthesis is initiated.

As noted above, the present invention provides materials and methods for use in producing thrombopoietin in a homogeneous form. The TPO of the present invention is characterized by an $M_r=70,000\pm10,000$ daltons as determined by SDS-polyacrylamide gel electrophoresis under denaturing conditions. The TPO of the present invention is provided at least 90% pure with respect to other contaminating proteins as determined by SDS-polyacrylamide gel electrophoresis and silver staining. Within a preferred embodiment, the protein is essentially free of lower molecular weight forms of TPO (i.e. those exhibiting an $M_r<55$ kD) as determined by "Western" blot analysis (Towbin et al., *Proc. Natl. Acad Sci. USA* 76: 4350–4354, 1979; Towbin et al., U.S. Pat. No. 4,452,901, incorporated herein by reference in their entirety) using polyclonal antisera directed against the N-terminus of TPO. By "essentially free" is meant that not more than 5% of the immunoreactive TPO is in the lower molecular weight range.

As noted above, thrombopoietin was identified as a protein that stimulates cell growth via the MPL receptor. This receptor (Souyri et al., *Cell* 63:1137–1147, 1990) was, prior to this discovery, an "orphan" receptor whose natural ligand was unknown. Recombinant TPO has been found to stimulate the proliferation and differentiation of megakaryocytes.

Thrombopoietin molecules are characterized by their ability to specifically bind to MPL receptor from the same species and to stimulate platelet production in vivo. In normal test animals, TPO is able to increase platelet levels by 100% or more within 10 days after beginning daily administration. The term "thrombopoietin" as used herein encompasses full-length thrombopoietin molecules and biologically active portions thereof, that is fragments of a thrombopoietin that exhibit the qualitative biological activities of the intact molecule (receptor binding and in vivo stimulation of platelet production).

The sequences of cDNA clones encoding representative mouse and human TPO proteins are shown in SEQ ID NO: 1 and SEQ ID NO:3, respectively, and the corresponding amino acid sequences are shown in SEQ ID NO: 2 and SEQ ID NO:4, respectively. Those skilled in the art will recognize that the sequences shown in SEQ ID NOS: 1, 2, 3 and 4 correspond to single alleles of the murine or human gene, and that allelic variation is expected to exist. Allelic variants of the DNA sequences shown in SEQ ID NO: 1 and SEQ ID NO:3 include those containing silent mutations and those in which mutations result in amino acid sequence changes. It will also be evident that one skilled in the art could create additional variants, such as by engineering sites that would facilitate manipulation of the nucleotide sequence using alternative codons.

Analysis of amino acid sequences indicates that the mature proteins extend from amino acid residue 45 (Ser) to residue 379 (Thr) of SEQ ID NO: 2 (residues 22–353 of SEQ ID NO: 4). The predicted amino terminus of the human protein corresponds precisely to the demonstrated mature amino terminus for recombinant murine TPO (Lok et al., ibid.).

The murine and human sequences disclosed herein are useful tools for preparing isolated polynucleotide molecules encoding TPO proteins from other species ("species homologs"). Preferred such species homologs include mammalian homologs such as bovine, canine, porcine, ovine, equine and, in particular, primate proteins. Methods for using sequence information from a first species to clone a corresponding polynucleotide sequence from a second species are well known in the art. See, for example, Ausubel et al., eds., *Current Protocols in Molecular Biology*, John Wiley and Sons, Inc., N.Y., 1987.

Analysis of mRNA distribution showed that mRNA encoding TPO was present in several tissues of human and mouse, and was more abundant in lung, liver, heart, skeletal muscle and kidney. Thus, to isolate homologs from other species, a cDNA library is prepared, preferably from one of the tissues found to produce higher levels of the mRNA. Methods for preparing cDNA libraries are well known in the art. See, for example, Sambrook et al., eds., *Molecular Cloning: A Laboratory Manual*, 2nd ed., Cold Spring Harbor Laboratory Press, 1989 and references cited therein. To detect molecules encoding TPO, the library is then probed with a mouse or human DNA sequence disclosed herein or with a fragment thereof or with one or more small probes based on the disclosed sequences. Of particular utility are probes comprising an oligonucleotide of at least about 14 or more nucleotides and up to 25 or more nucleotides in length that are at least 80% identical to a same-length portion of SEQ ID NO: 1, SEQ ID NO: 3, SEQ ID NO:5 or their complementary sequences. It is preferred to probe the library at a low hybridization stringency, i.e. about 2× SSC and a hybridization temperature of about 50° C. using labeled probes. Molecules to which the probe hybridizes are detected using standard detection procedures. Positive clones are confirmed by sequence analysis and activity assays, such as ability to bind homologous MPL receptor (i.e. an MPL receptor from the same species as the cDNA) or to stimulate megakaryopoiesis from homologous marrow cells. As will be evident to one skilled in the art, other cloning methods can be utilized.

TPO proteins are substantially homologous to the proteins of SEQ ID NO: 2 or SEQ ID NO:4 and their species homologs. The term "substantially homologous" is used herein to denote proteins having 50%, preferably 60%, more preferably at least 80%, sequence identity to the sequences shown in SEQ ID NO: 2 or SEQ ID NO:4 or their species homologs. Such proteins will more preferably be at least 90% identical, and most preferably 95% or more identical to SEQ ID NO: 2 or SEQ ID NO:4 or their species homologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 1

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| A | 4  |    |    |    |    |    |    |    |    |    |    |    |    |    |    |    |    |    |    |   |
| R | -1 | 5  |    |    |    |    |    |    |    |    |    |    |    |    |    |    |    |    |    |   |
| N | -2 | 0  | 6  |    |    |    |    |    |    |    |    |    |    |    |    |    |    |    |    |   |
| D | -2 | -2 | 1  | 6  |    |    |    |    |    |    |    |    |    |    |    |    |    |    |    |   |
| C | 0  | -3 | -3 | -3 | 9  |    |    |    |    |    |    |    |    |    |    |    |    |    |    |   |
| Q | -1 | 1  | 0  | 0  | -3 | 5  |    |    |    |    |    |    |    |    |    |    |    |    |    |   |
| E | -1 | 0  | 0  | 2  | -4 | 2  | 5  |    |    |    |    |    |    |    |    |    |    |    |    |   |
| G | 0  | -2 | 0  | -1 | -3 | -2 | -2 | 6  |    |    |    |    |    |    |    |    |    |    |    |   |
| H | -2 | 0  | 1  | -1 | -3 | 0  | 0  | -2 | 8  |    |    |    |    |    |    |    |    |    |    |   |
| I | -1 | -3 | -3 | -3 | -1 | -3 | -3 | -4 | -3 | 4  |    |    |    |    |    |    |    |    |    |   |
| L | -1 | -2 | -3 | -4 | -1 | -2 | -3 | -4 | -3 | 2  | 4  |    |    |    |    |    |    |    |    |   |
| K | -1 | 2  | 0  | -1 | -3 | 1  | 1  | -2 | -1 | -3 | -2 | 5  |    |    |    |    |    |    |    |   |
| M | -1 | -1 | -2 | -3 | -1 | 0  | -2 | -3 | -2 | 1  | 2  | -1 | 5  |    |    |    |    |    |    |   |
| F | -2 | -3 | -3 | -3 | -2 | -3 | -3 | -3 | -1 | 0  | 0  | -3 | 0  | 6  |    |    |    |    |    |   |
| P | -1 | -2 | -2 | -1 | -3 | -1 | -1 | -2 | -2 | -3 | -3 | -1 | -2 | -4 | 7  |    |    |    |    |   |
| S | 1  | -1 | 1  | 0  | -1 | 0  | 0  | 0  | -1 | -2 | -2 | 0  | -1 | -2 | -1 | 4  |    |    |    |   |
| T | 0  | -1 | 0  | -1 | -1 | -1 | -1 | -2 | -2 | -1 | -1 | -1 | -1 | -2 | -1 | 1  | 5  |    |    |   |
| W | -3 | -3 | -4 | -4 | -2 | -2 | -3 | -2 | -2 | -3 | -2 | -3 | -1 | 1  | -4 | -3 | -2 | 11 |    |   |
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 |

Substantially homologous proteins are characterized as having one or more amino acid substitutions, deletions or additions. These changes are preferably of a minor nature, such as conservative amino acid substitutions that do not significantly affect the folding or activity of the protein (see Table 2). See, in general Ford et al., *Protein Expression and Purification* 2: 95–107, 1991, which is incorporated herein by reference.

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |

TABLE 2-continued

Conservative amino acid substitutions

| | |
|---|---|
| | tyrosine |
| Small: | glycine |
| | alanine |
| | serine |
| | threonine |
| | methionine |

Essential amino acids in TPO can be identified according to procedures known in the art, such as site-directed mutagenesis or alanine-scanning mutagenesis (Cunningham and Wells, *Science* 244, 1081–1085, 1989). In the latter technique, single alanine mutations are introduced at every residue in the molecule, and the resultant mutant molecules are tested for biological activity (e.g. receptor binding, in vitro or. in vivo proliferative activity) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., *Science* 255:306–312, 1992; Smith et al., *J. Mol. Biol.* 224:899–904, 1992; Wlodaver et al., *FEBS Lett.* 309:59–64, 1992.

In general, cytokines are predicted to have a four-alpha helix structure, with the first and fourth helices being most important in ligand-receptor interactions and more highly conserved among members of the family. Referring to the human TPO amino acid sequence shown in SEQ ID NO:4, alignment of cytokine sequences suggests that these helices are bounded by amino acid residues 29 and 53, 80 and 99, 108 and 130, and 144 and 168, respectively (boundaries are ±4 residues). Helix boundaries of the mouse (SEQ ID NO:2) and other non-human TPOs can be determined by alignment with the human sequence. Other important structural aspects of TPO include the cysteine residues at positions 51, 73, 129 and 195 of SEQ ID NO:2 (corresponding to positions 28, 50, 106 and 172 of SEQ ID NO:4).

Within the present invention, thrombopoietin can be prepared from a variety of sources, including blood, plasma, urine, cell culture media and milk. It is generally preferred to produce TPO as a recombinant protein in genetically engineered cultured cells or multicellular organisms. The protein is then purified from cell lysates or extracts, conditioned culture media, or, in the case of multicellular organisms, milk or other fluid.

Thrombopoietin can be produced in genetically engineered cultured cells according to conventional techniques. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., ibid., which are incorporated herein by reference.

In general, a DNA sequence encoding a TPO protein is operably linked to a transcription promoter and terminator within an expression vector. The vector will commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct TPO into the secretory pathway of the host cells, a secretory signal sequence (also known as a leader sequence, prepro sequence or pre sequence) is provided in the expression vector. The secretory signal sequence is joined to the DNA sequence encoding a protein of the present invention in the correct reading frame. Secretory signal sequences are commonly positioned 5' to the DNA sequence encoding the protein of interest, although certain signal sequences may be positioned elsewhere in the DNA sequence of interest (see, e.g., Welch et al., U.S. Pat. No. 5,037,743; Holland et al., U.S. Pat. No. 5,143,830). The secretory signal sequence may be one normally associated with TPO, or may be from a gene encoding another secreted protein, such as a tissue-type plasminogen activator.

Expression vectors for mouse and human TPO have been prepared and deposited with American Type Culture Collection, 12301 Parklawn Drive, Rockville, Md. under the provisions of the Budapest Treaty. Vector pZGmpl-1081 (ATCC 69566) contains a mouse TPO cDNA linked to an adenovirus major late promoter. Vector pZGmpl-124 (ATCC 69615) contains a human TPO cDNA linked to a mouse metallothinein promoter and an hGH terminator, and a DHFR selectable marker.

Yeast cells, particularly cells of the genus Saccharomyces, are a preferred host for use in producing recombinant TPO. Methods for transforming yeast cells with exogenous DNA and producing recombinant proteins therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. A preferred secretory signal sequence for use in yeast is that of the *S. cerevisiae* MFα1 gene (Brake, ibid.; Kurjan et al., U.S. Pat. No. 4,546,082). Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii* and *Candida maltosa* are known in the art. See, for example, Gleeson et al., *J. Gen. Microbiol.* 132:3459–3465, 1986; Cregg, U.S. Pat. No. 4,882,279; and Stroman et al., U.S. Pat. No. 4,879,231.

Other fungal cells are also suitable as host cells. For example, Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., NY, 1987), and cationic lipid-mediated transfection (Hawley-Nelson et al., *Focus* 15:73–79, 1993), which are incorporated herein by reference. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601, 978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate (MTX). Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign proteins therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci.* (*Bangalore*) 11:47–58, 1987.

Preferred prokaryotic host cells are strains of the bacteria *Escherichia coli*, although Bacillus and other genera are also useful. Techniques for transforming these hosts and expressing foreign DNA sequences cloned therein are well known in the art (see, e.g., Sambrook et al., ibid.). When expressing the proteins in bacteria such as *E. coli*, the protein may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate. The denatured protein is then refolded by diluting the denaturant. In the latter case, the protein can be recovered from the periplasmic space in a soluble and functional form by disrupting the cells (by, for example, sonication or osmotic shock) to release the contents of the periplasmic space and recovering the protein.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Transgenic animal technology may also be employed to produce TPO. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (from about 1 to 15 g/l).

From a commercial point of view, it is clearly preferable to use as the host a species that has a large milk yield. While smaller animals such as mice and rats can be used (and are preferred at the proof-of-concept stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk. See WIPO Publication WO 88/00239 for a comparison of factors influencing the choice of host species. It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489, incorporated herein by reference), β-lactoglobulin, α-lactalbumini, and whey acidic protein. The β-lactoglobulin (BLG) promoter is preferred. In the case of the ovine β-lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non-coding portion of the β-lactoglobulin gene. See Whitelaw et al., *Biochem J.* 286: 31–39, 1992. Similar fragments of promoter DNA from other species are also suitable.

General procedures for producing transgenic animals are known in the art. See, for example, Hogan et al., *Manipulatina the Mouse Embryo: A Laboratory Manual*, Cold Spring Harbor Laboratory, 1986; Simons et al., *Bio/Technology* 6: 179–183, 1988; Wall et al., *Biol. Reprod.* 32: 645–651, 1985; Buhler et al., *Bio/Technology* 8: 140–143, 1990; Ebert et al., *Bio/Technology* 9: 835–838, 1991; Krimpenfort et al., *Bio/Technology* 9: 844–847, 1991; Wall et al., *J. Cell. Biochem.* 49: 113–120, 1992; U.S. Pat. Nos. 4,873,191 and 4,873,316; WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., *Proc. Natl. Acad. Sci. USA* 77: 7380–7384, 1980; Gordon and Ruddle, *Science* 214: 1244–1246, 1981; Palmiter and Brinster, *Cell* 41: 343–345, 1985; Brinster et al., *Proc. Natl. Acad. Sci. USA* 82: 4438–4442, 1985; and Hogan et al. (ibid.). These techniques were subsequently adapted for use with larger animals, including livestock species (see e.g., WIPO publications WO 88/00239, WO 90/05188, and WO 92/11757; and Simons et al., *Bio/Technology* 6: 179–183, 1988). To summarize, in the most efficient route used to date in the generation of transgenic mice or livestock, several hundred linear molecules of the DNA of interest are injected into one of the pro-nuclei of a fertilized egg according to techniques which have become standard in the art. Injection of DNA into the cytoplasm of a zygote can also be employed.

Production in transgenic plants may also be employed. Expression may be generalized or directed to a particular organ, such as a tuber. See, Hiatt, *Nature* 344:469–479, 1990; Edelbaum et al., *J. Interferon Res.* 12:449–453, 1992; Sijmons et al., *Bio/Technology* 8:217–221, 1990; European Patent Office Publication EP 255,378; and Hiatt et al., U.S. Pat. No. 5,202,422.

According to the present invention, TPO is purified using a combination of methods including affinity purification and separation based on charge of the protein. Affinity purification is carried out on an immobilized MPL receptor protein or ligand-binding portion thereof, and the bound TPO is eluted and subjected to further fractionation by conventional methods.

As noted above, it is preferred to- purify thrombopoietin from a fluid such as conditioned cell culture media, milk or a fraction thereof. In general, genetically engineered cells and organisms are more cost-effective than "natural" sources (e.g. blood, plasma, urine) of proteins, and provide a production system that is easier to control and monitor.

To reduce the time required for fractionation it is preferred to first concentrate the TPO in the biological fluid. Concentration can be achieved by any of a number of means known in the art. Preferred methods of concentration include ultrafiltration using a membrane having a molecular weight cutoff between about 10 kD and about 30 kD, and direct capture on an absorbant such as a dye resin (e.g., Mimetic Green™, Lexton Scientific International, Signal Hill, Calif.).

The thrombopoietin-containing biological fluid is applied to a polypeptide comprising a ligand-binding domain of an MPL receptor, which polypeptide is bound to a solid support. MPL receptors have been described in the scientific literature. See, for example, Vigon et al., *Proc. Natl. Acad. Sci. U.S.A.* 89: 5640–5644, 1992 and Skoda et al., *EMBO J.* 12: 2645–2653, 1993. The amino acid sequence of the N-terminal extracellular domain of a mouse MPL receptor is shown in SEQ ID NO: 7. Those skilled in the art will recognize that SEQ ID NO: 7 is representative of a single allele of mouse MPL receptor, and that allelic variation is expected to exist. MPL receptors from other species (e.g. human or other primate, rat, dog, pig, etc.) can be identified by function and structural similarity to the mouse receptor. The ligand binding domain of the mouse MPL receptor is contained within the extracellular portion of the protein (residues 27 to 480 of SEQ ID NO: 7), with residues 293–297, 358–361, and 398–419 believed to be of particular importance for ligand binding. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

Within a preferred embodiment of the invention, the receptor polypeptide bound to a solid support is provided in the form of a column. The biological fluid is passed over the column under conditions that favor adsorption of TPO onto the receptor (e.g. in a pH 7.0–9.0 buffer containing 0–1.0 M NaCl). The column is then washed to remove unadsorbed material. Suitable washing conditions will be evident to those skilled in the art. It is preferred to wash with a buffered, neutral to slightly basic solution of low to moderate salt concentration, such as a pH 7.0 to 9.0 Tris-buffered solution containing 0.5 to 1.0 M NaCl. The adsorbed TPO is then eluted from the receptor polypeptide. Elution is carried out by washing the receptor-TPO complex with chaotropic agents such as KSCN, urea, or guanidine HCl, preferably 2.0 to 3.5 M KSCN.

In the alternative, TPO can be adsorbed to a receptor polypeptide in a batch fashion. In a typical procedure, the receptor polypeptide is bound to insoluble particles (e.g. resin beads) and incubated with a solution containing TPO for 2–24 hours. TPO bound to the immobilized polypeptide is removed from solution, such as by gentle centrifugation or filtration. The receptor polypeptide particles are then washed with a buffered solution as generally disclosed above, and TPO is eluted from the polypeptide with a chaotropic agent. Elution may be carried out in a batch fashion by adding a chaotropic agent to release TPO from the polypeptide followed by centrifuging to separate the soluble TPO from the insoluble receptor polypeptide particles. In an alternative process, the particle-receptor polypeptide-TPO complex is poured into a column, and the TPO is eluted as disclosed above.

Prior to additional purification, it is preferred to remove the eluant from the eluted TPO. Suitable methods for removal include dialysis, gel filtration and direct capture, with dialysis preferred. Selection of a dialysis buffer is within the level of ordinary skill in the art. Weakly alkaline, buffered solutions are preferred.

The TPO-containing solution may then be fractionated, such as by anion exchange chromatography. Preferred chromatographic media include anion exchange matrices having quaternary amine or diethylaminoethyl groups such as Mono Q®, Q-Sepharose® and DEAE Sepharose® (available from Pharmacia Biotech, Piscataway, N.J.). Prior to elution, the column is washed with a low ionic strength buffer such as 0.025 M Tris-HCL, pH 8.5. TPO is eluted from the column by applying a salt gradient, such as 0 to 0.5 M NaCl in pH 8.5 Tris buffer. TPO elutes at a salt concentration between about 0.05 and 0.15 M.

Purification is monitored by, conventional methods, such as spectrophotometrically or electrophoretically. Electrophoresis on SDS-polyacrylamide gels using silver staining and "Western" blotting is a preferred method of monitoring purification.

A typical anion exchange fractionation is illustrated in FIG. 1. TPO is separated into low (18,000–55,000 daltons) and high (70,000±10,000 daltons) molecular weight species. Fractions of highly purified TPO are then pooled, providing, in one embodiment, a preparation of TPO having a $M_r$=70,000±10,000 daltons that is essentially free of TPO species of $M_r$<55 kD.

Proteins prepared according to the present invention can be used therapeutically wherever it is desirable to increase proliferation of cells in the bone marrow, such as in the treatment of cytopenia, such as that induced by aplastic anemia, myelodisplastic syndromes, chemotherapy or congenital cytopenias; and in the treatment of anemia. The proteins are particularly useful for increasing platelet production, such as in the treatment of thrombocytopenia. Thrombocytopenia is associated with a diverse group of diseases and clinical situations that may act alone or in concert to produce the condition. Lowered platelet counts can result from, for example, defects in platelet production, abnormal platelet distribution, dilutional losses due to massive transfusions, or abnormal destruction of platelets. For example, chemotherapeutic drugs used in cancer therapy may suppress development of platelet progenitor cells in the bone marrow, and the resulting thrombocytopenia limits the chemotherapy and may necessitate transfusions. In addition, certain malignancies can impair platelet production and platelet distribution. Radiation therapy used to kill malignant cells also kills platelet progenitor cells. Thrombocytopenia may also arise from various platelet autoimmune disorders induced by drugs, neonatal alloimmunity or platelet transfusion alloimmunity. The proteins of the present invention can reduce or eliminate the need for transfusions, thereby reducing the incidence of platelet alloimmunity. Abnormal destruction of platelets can result from: (1) increased platelet consumption in vascular grafts or traumatized tissue; or (2) immune mechanisms associated with, for example, drug-induced thrombocytopenia, idiopathic thrombocytopenic purpura (ITP), autoimmune diseases, hematologic disorders such as leukemia and lymphoma or metastatic cancers involving bone marrow. Other indications for the proteins of the present invention include aplastic anemia and drug-induced marrow suppression resulting from, for example, chemotherapy or treatment of HIV infection with AZT.

Thrombocytopenia is manifested as increased bleeding, such as mucosal bleedings from the nasal-oral area or the gastrointestinal tract, as well as oozing from wounds, ulcers or injection sites.

Compositions of TPO have also been found effective for increasing the level of circulating erythrocytes and erythrocyte precursor cells. Reduction in the circulating levels of these cells are known as anemia. The erythrocyte level in blood is measured as the amount of hemoglobin per 100 ml or as the volume of packed red blood cells per 100 ml of blood. Patients are diagnosed as anemic if their hematocrit levels fall below 11–13 gm/100 ml of blood (depending upon the age and sex of the patient). TPO is particularly useful for treatment of anemias associated with bone marrow failure, where a decrease in blood cell formation is associated with, for example, the toxic effects of chemotherapy. In addition, certain malignancies can impair platelet and erythrocyte production and distribution. Radiation therapy used to kill malignant cells also kills platelet and erythroid progenitor cells. Abnormal destruction of platelets and erythrocytes can result from hematologic disorders such as leukemia and lymphoma or metastatic cancers involving bone marrow. Other indications for the proteins of the present invention to treat concurrent anemia and thrombocytopenia include aplastic anemia and drug-induced marrow suppression resulting from, for example, chemotherapy or treatment of HIV infection with AZT. In this regard, TPO can be administered alone or in combination with erythropoietin.

For pharmaceutical use, TPO is formulated for parenteral, particularly intravenous or subcutaneous, delivery according to conventional methods. Intravenous administration will be by bolus injection or infusion over a typical period of one to several hours. In general, pharmaceutical formulations will include TPO in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. In addition, TPO may be combined with other cytokines, particularly early-acting cytokines such as stem cell factor, IL-3, IL-6, IL-11 or GM-CSF. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses of the TPO of the present invention will generally be in the range of 0.1 to 100 µg/kg of patient weight per day, preferably 0.5–50 µg/kg per day, with the exact dose determined by the clinician according to accepted standards, taking into account the nature and severity of the condition to be treated, patient traits, etc. In certain cases, such as when treating patients showing increased sensitivity or requiring prolonged treatment, doses in the range of 0.1–20 µg/kg per day will be indicated. Determination of dose is within the level of ordinary skill in the art. TPO will commonly be administered over a period of up to 28 days following chemotherapy or bone-marrow transplant or until a platelet count of >20,000/mm$^3$, preferably >50,000/mm$^3$, is achieved. More commonly, TPO will be administered over one week or less, often over a period of one to three days. In general, a therapeutically effective amount of TPO is an amount sufficient to produce a clinically significant increase in the proliferation and/or differentiation of myeloid progenitor cells, which will be manifested as an increase in circulating levels of platelets or erythrocytes. Treatment of platelet disorders will thus be continued until a platelet count of at least 20,000/mm$^3$, preferably 50,000/mm$^3$, is reached. Treatment of anemia will be continued until a normal hematocrit is restored. TPO can also be administered in combination with other cytokines such as IL-3, -6 and -11; stem cell factor; erythropoietin; G-CSF and GM-CSF. Within regimens of combination therapy, daily doses of other cytokines will in general be: EPO, ≦150 U/kg; GM-CSF, 5–15 µg/kg; IL-3, 1–5 µg/kg; and G-CSF, 1–25 µg/kg. Combination therapy with EPO, for example, is indicated in anemic patients with low EPO levels.

TPO is also a valuable tool for the in vitro study of the differentiation and development of hematopoietic cells, such as for elucidating the mechanisms of cell differentiation and for determining the lineages of mature cells, and may also find utility as a proliferative agent in cell culture.

TPO can also be used ex vivo, such as in autologous marrow culture. Briefly, bone marrow is removed from a patient prior to chemotherapy and treated with TPO, optionally in combination with one or more other cytokines. The treated marrow is then returned to the patient after chemotherapy to speed the recovery of the marrow. In addition, TPO can also be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors can be collected and concentrated from peripheral blood and then treated in culture with TPO, optionally in combination with one or more other cytokines, including but not limited to SCF, G-CSF, IL-3, GM-CSF, IL-6 or IL-11, to differentiate and proliferate into high-density megakaryocyte cultures, which can then be returned to the patient following high-dose chemotherapy.

The invention is further illustrated by the following non-limiting examples.

EXAMPLES

Example 1

Cloning of a Human TPO Gene

An amplified human lung Lambda FIX® genomic library (Stratagene Cloning Systems, La Jolla, Calif.) was screened for the gene encoding human thrombopoietin using a mouse TPO cDNA (Lok et al., ibid. and SEQ ID NO: 1) as a probe. The library was titered, and 30 150-mm plates inoculated with *E. coli* strain LE-392 cells (Stratagene Cloning Systems) were infected with 4×10$^4$ plaque forming units (PFU). The plates were incubated overnight at 37° C. Filter plaque lifts were made using HYBOND-N™ nylon membranes (Amersham Corp,. Arlington Heights, Ill.) according to the procedure recommended by the manufacturer. The filters were processed by denaturation in a solution containing 1.5 M NaCl and 0.5 M NaOH for 7 minutes at room temperature. The filters were blotted briefly on filter paper to remove excess denaturation solution followed by neutralization for 5 minutes in 1 M Tris-HCl (pH 7.5) and 1.5 M NaCl. Phage DNA was fixed onto the filters with 1,200 μJoules of UV energy in a STRATALINKER® UV crosslinker (Stratagene Cloning Systems). After fixing, the filters were prewashed three times in 0.25×SSC, 0.25% SDS and 1 mM EDTA at 65° C. After prewashing, the filters were prehybridized in hybridization solution (5× SSC, 5× Denhardt's solution, 0.2% SDS and 1 mM EDTA) that had been filtered through a 0.45 μM filter. Heat denatured, sheared salmon sperm DNA (final concentration 100 μg/mL) was added immediately before use. The filters were prehybridized at 65° C. overnight.

Full length mouse TPO cDNA from pZGmpl-1081 (deposited with American Type Culture Collection, 12301 Parklawn Drive, Rockville, Md. as an *E. coli* DH5α transformant on Feb. 14, 1994 and assigned accession number ATCC 69566) was labeled with $^{32}$P by random priming using the MEGAPRIME™ DNA Labeling System (Amersham) according to the method recommended by the manufacturer. The prehybridization solution was replaced with fresh hybridization solution containing approximately $1 \times 10^6$ cpm probe and allowed to hybridize overnight at 65° C. After hybridization, the hybridization solution was removed, and the filters were rinsed four or five times each in a wash solution containing 0.25× SSC, 0.25% SDS, and 1 mM EDTA. After rinsing, the filters were washed in eight consecutive washes at 50° C. in wash solution. Following the final wash, the filters were exposed to autoradiograph film (XAR-5; Eastman Kodak Co.; Rochester, N.Y.) for four days at −70° C. with an intensifying screen.

Examination of the autoradiographs revealed several hundred regions that hybridized with the labeled probe. Agar plugs were picked from 100 regions for purification. Each agar plug was soaked overnight in 1 ml of SM (containing, per liter, 5.8 g NaCl, 2 g MgSO$_4$.7H$_2$O, 50 ml 1 M Tris-Cl, pH 7.5, 5 ml 2% gelatin; Maniatis et al., eds., *Molecular Cloning: A Laboratory Manual*, Cold Spring Harbor, N.Y., 1982) containing 1% (v/v) chloroform. After the overnight incubation, the phage from each plug were diluted 1:1,000 in SM. Aliquots of 5 μl were plated on *E. coli* strain LE392 cells. The plates were incubated overnight at 37° C., and filter lifts were prepared, prehybridized, hybridized, washed and autoradiographed as described above.

Examination of the resulting autoradiographs revealed strong positive signals from two primary isolates and weak signals from eighteen others. Agar plugs were picked from the positive areas for each of the twenty signals. The agar plugs were treated as described above. The phage eluted from each agar plug were diluted 1:100 in SM, and aliquots of 1 μl were plated with *E. coli* strain LE392 cells. The plates were incubated, and phage filter lifts were prepared and hybridized as described above. The filters were washed at 55° C. in wash buffer. Autoradiographs of the filters revealed areas of hybridization corresponding to single, discrete phage plaques from three original isolates, 8-3-2, 10-1-1 and 29-2-1.

Phage isolates 8-3-2, 10-1-1 and 29-2-1 were given the designations λZGmpl-H8, λGmpl-H10 and λZGmpl-H29, respectively. DNA from isolates λZGmpl-H8, λGmpl-H10 and λZGmpl-H29 was purified using LAMBDASORB™ phage adsorbent (Promega Corp., Madison, Wis.) according to the directions of the manufacturer. Human genomic DNA inserts from the phage were separated from phage vector DNA by digestion with Xba I and purified by agarose gel electrophoresis. All three phage isolates contained sequences which hybridized to the mouse mpl receptor ligand cDNA probe as shown by Southern blot analysis (Maniatis et al., ibid.). Phage λZGmpl-H8 was analyzed, and the hybridizing regions of λZGmpl-H8 were found to reside on three Xba I DNA fragments of 9.5 kb, 2.5 kb and 1 kb in length. The 2.5 kb fragment was subcloned into Xba I digested BLUESCRIPT® II SK+ phagemid (Stratagene Cloning Systems), to yield the plasmid pZGmpl-H82.5.

The sequence of the human TPO gene and the encoded amino acid sequence are shown in SEQ ID NO: 5 and SEQ ID NO: 6.

Example 2

Cloning of Human TPO cDNA

A full-length human TPO-encoding cDNA was isolated by polymerase chain reaction from human liver and kidney cDNA templates employing specific primers derived from exon sequences identified on pZGmpl-H82.5 and from conserved 5' untranslated sequence of the mouse TPO cDNA.

Human kidney, liver and lung poly d(T) selected poly(A)$^+$ RNAs (Clontech, Palo Alto, Calif.) were used to synthesize first strand cDNA. Each reaction mixture was prepared using four micrograms poly(A)$^+$ RNA mixed with 1 μg of oligo d(T)$_{18}$ (No 5' Phosphate) mRNA primer (New England Biolabs, Beverly, Mass.) in a final volume of 19 μl. The mixtures were heated to 65° C. for five minutes and cooled by chilling on ice. cDNA synthesis was initiated by the addition of 8 μl of 5× SUPERSCRIPT™ buffer (GIBCO BRL, Gaithersburg, Md.), 2 μl of 100 mM dithiothreitol, 2 μl of a deoxynucleotide triphosphate solution containing 10 mM each of dATP, dGTP, dTTP and dCTP (Pharmacia LKB Biotechnology Inc., Piscataway, N.J.), 2 μl of 1 μCi/μl $^{32}$p-α-dCTP (Amersham Corp., Arlington Heights, Ill.) and 8 μl of 200 U/μl SUPERSCRIPT™ reverse transcriptase (GIBCO BRL) to each of the RNA-primer mixtures. The reactions were incubated at 45° C. for 1 hour and were diluted to 120 μl with TE (10 mM Tris-HCl, pH 8.0, 1 mM EDTA). The cDNAs were precipitated twice by the addition of 50 μl 8 M ammonium acetate and 160 μl of isopropanol. The resulting cDNA pellets were resuspended in 10 μl of TE. The yield of first strand cDNA for each reaction was estimated from the levels of $^{32}$P-dCTP incorporation.

First strand cDNA from the liver, lung and kidney mRNA were used to generate two cDNA segments, an N-terminal one-third and the C-terminal two-thirds of the sequence, using separate polymerase chain reactions. A Kpn I restriction site was introduced into the cDNA segments by a single base change from the genomic sequence by PCR mutagenesis employing primers ZC7422 (SEQ ID NO: 8) and ZC7423 (SEQ ID NO: 9). The resulting nucleotide change created a common KpnI restriction site without alteration in the predicted amino acid coding.

The N-terminal segment was amplified in a 50 μl reaction containing 5 ng of template cDNA (in separate reactions for kidney, liver and lung cDNAs), 80 pmoles each of oligonucleotides ZC7424 (SEQ ID NO: 10) and ZC7422 (SEQ ID NO: 8), 5 μl of 2.5 mM deoxynucleotide triphosphate solution (Cetus Corp., Emeryville, Calif.), 5 μl of 10× PCR buffer (Promega Corp., Madison, Wis.) and 2.5 units of Taq polymerase (Boehringer Mannheim Inc., Indianapolis, Ind.). The polymerase chain reaction was run for 35 cycles (1 minute at 94° C., 1 minute at 58° C. and 1.5 minute at 72°

C.) followed by a 7 minute incubation at 72° C. Sense primer ZC7424 (SEQ ID NO:10) spanned the mouse MPL receptor ligand 5' nontranslated region and included the ATG initiation codon. Antisense primer ZC7422 (SEQ ID NO:8) included sequence from the region corresponding to exons 4 and 5 of the human genomic TPO DNA.

The C-terminal segment was amplified in a 50 μl reaction mixture containing 5 ng of template cDNA (human kidney, liver or lung as described above), 80 pmoles each of oligonucleotides ZC7423 (SEQ ID NO:9) and ZC7421 (SEQ ID NO:11), 5 μl of 2.5 mM deoxynucleotide triphosphate solution (Cetus Corp.), 5 μl of 10× PCR buffer (Promega Corp.) and 2.5 units of Taq polymerase (Boehringer Mannheim, Inc.). The polymerase chain reaction was run for 35 cycles (1 minute at 94° C., 1 minute at 65° C. and 1.5 minutes at 72° C.) followed by a 7 minute incubation at 72° C. Sense primer ZC7423 (SEQ ID NO: 9) included sequence from regions corresponding to exons 4 and 5 of the human genomic TPO DNA. Antisense primer ZC7421 (SEQ ID NO:11) included sequence from the region corresponding to the 3' noncoding sequence of the human gene and included the translation termination codon.

The amplified PCR products were analyzed by direct DNA sequencing and were subcloned into PGEM-T (Promega Corp.) for further analysis by comparison to the mouse cDNA sequence and to human genomic sequences. A DNA sequence encoding human TPO is shown in SEQ ID NO: 3, and the encoded amino acid sequence is shown in SEQ ID NO: 4. Sequence analysis indicates that signal peptide cleavage occurs following Ser21 (SEQ ID NO: 4) and the mature protein begins at amino acid 22 (SEQ ID NO: 4).

The human N-terminal and C-terminal PCR fragments were excised from pGEM-T as EcoRI-KpnI fragments and ligated into the EcoRI site of expression vector Zem229R. This plasmid was transfected into BHK 570 cells using Lipofectamine™ (GIBCO BRL). 24 hours after transfection, the culture medium (DMEM+PSN+10% FCS) was replaced with fresh medium, and the cells were incubated for 48 hours in the absence of selective agents. Conditioned medium was assayed for proliferative activity using the BaF3/MPLR1.1 cell line (deposited Sep. 28, 1994 under the terms of the Budapest Treaty with American Type Culture Collection, 12301 Parklaan Drive, Rockville, Md. and assigned accession number CRL 11723). Briefly, conditioned culture medium was added to 100 μl of $10^6$/ml washed BaF3/MPLR1.1 cells in RPMI 1640 media (JRH Bioscience Inc., Lenexa, Kans.) supplemented with 2 mM L-glutamine, PSN antibiotics (GIBCO BRL), 0.00036% 2-mercaptoethanol and 10% heat-inactivated fetal calf serum. The cells were incubated for 3 days at 37° C. under 5% $CO_2$ before assaying for proliferation. Cell proliferation in the presence of TPO was quantified using a calorimetric assay based on the metabolic breakdown of 3-(4,5-dimethylthiazol-2-yl)-2,5-diphenyl tetrazolium bromide (MTT) (Mosman, *J. Immunol. Meth.* 65: 55–63, 1983). Twenty μl of a 10 mg/ml solution of MTT (Polyscience, Inc., Warrington, Pa.) was added to 100 μl of BaF3/MPLR1.1 assay cells, and the cells were incubated at 37° C. After 4 hours, 200 μl of 0.04 N HCl in isopropanol was added, the solution was mixed, and the absorbance of the sample was read at 570 nm on a model EL320 ELISA reader (Bio-Tek Instruments Inc., Highland Park, Vt.). The results clearly showed that the human TPO in the culture medium stimulated the proliferation of the BaF3 cells expressing the mouse MPL receptor.

cDNA was made from both human liver and kidney mRNA (obtained from Clontech Laboratories, Inc.) using SUPERSCRIPT™ reverse transcriptase (GIBCO BRL) according to the manufacturer's specifications. Liver- and kidney-derived human TPO DNA clones were then made using two PCR reactions (conditions shown in Table 3). The reactions were run for 35 cycles at 94° C. for 1 minute, 58° C. for 1 minute, 72° C. for 1.5 minute; followed by a 7 minute incubation at 72° C.

Table 3

Reaction #1:
  5 ng liver or kidney cDNA
  4 μl oligonucleotide ZC7454 (20 pM/μl) (SEQ ID NO:12; introduces an EcoRI site 5' of the ATG)
  4 μl oligonucleotide ZC7422 (20 pM/μl) (SEQ ID NO:8; creates an Asp718 site)
  5 μl dNTPs solution containing 2.5 mM dATP, 2.5 mM dGTP, 2.5 mM dCTP and 2.5 mM dTTP
  5 μl 10× Taq buffer (Boehringer Mannheim)
  1 μl Taq polymerase (Boehringer Mannheim) 30 μl $H_2O$ Table 3 (continued)

Reaction #2:
  5 ng liver or kidney cDNA
  4 μl oligonucleotide ZC7423 (20 pM/μl) (SEQ ID NO:9; creates an Asp718 site)
  4 μl oligonucleotide ZC7453 (20 pM/μl) (SEQ ID NO:13; creates an EcoRI site 3' of the TGA)
  5 μl dNTPs solution containing 2.5 mM dATP, 2.5 mM dGTP, 2.5 mM dCTP and 2.5 mM dTTP
  5 μl 10× Taq buffer (Boehringer Mannheim)
  1 μl Taq polymerase (Boehringer Mannheim) 30 μl $H_2O$ The PCR products were treated with phenol/chloroform/isoamyl alcohol and precipitated with 95% ETOH, dried, and resuspended in 20 μl $H_2O$. Each product was then cut with the restriction enzymes Asp718 and EcoRI and electrophoresed on a 1% agarose gel. 410 bp fragments (liver and kidney) from Reaction #1 and 699 bp fragments (liver and kidney) from Reaction #2 were excised from the gel and eluted by centrifugation of gel slabs through nylon wool. The PCR products of Reaction #1 and Reaction #2 were ligated together with the vector Zem229R (deposited with American Type Culture Collection, 12301 Parklawn Drive, Rockville, Md. on Sep. 28, 1993 under accession number 69447) which had been cut with EcoRI, thereby joining the two products at a created Asp718 site. The resultant plasmids were designated #10 (containing the kidney derived cDNA) and #28 (containing the liver derived cDNA).

Upon sequencing the DNAS, single PCR-generated errors were found 5' and 3' of a unique AvrII site in the #28 and #10 plasmids, respectively. To create an error-free TPO DNA, an 826 bp EcoRI-AvrII 5' fragment was isolated from #10 and a 283 bp AvrII-EcoRI 3' fragment was isolated from #28. The two fragments were ligated together with the vector Zem229R which had been cut with EcoRI. The resultant plasmid was designated pZGmpl-124. This plasmid was deposited with American Type Culture Collection, 12301 Parklawn Drive, Rockville, Md. on May 4, 1994 as an *E. coli* DH10b transformant under accession number 69615.

Example 3

Cloning of Human MPL Receptor cDNAs

Human MPL-P and MPL-K receptor isoform encoding cDNAs were isolated from human erythroid leukemic (HEL) cells (Martin and Papayannopoulu, *Science* 216: 1233–1235, 1982) by reverse transcriptase polymerase chain reaction (PCR) employing primers made according to the published sequence encoding the amino and carboxyl termini of the receptors (Vigon et al., *Proc. Natl. Acad. Sci. USA* 89: 5640–5644, 1992). Template HEL cell cDNA was synthesized from poly d(T)-selected poly(A)$^+$ RNA using primer ZC5499 (SEQ ID NO: 14). Thirteen Al of HEL cell poly(A)$^+$ RNA at a concentration of 1 µg/µl was mixed with 3 µl of 20 pmole/µl first strand primer ZC5499 (SEQ ID NO: 14). The mixture was heated at 65° C. for 4 minutes and cooled by chilling on ice.

First strand cDNA synthesis was initiated by the addition of 8 µl of first strand buffer (250 mM Tris-HCl, pH 8.3, 375 mM KCl, 15 mM MgCl$_2$) (5× SUPERSCRIPT™ buffer; GIBCO BRL), 4 µl of 100 mM dithiothreitol and 3 µl of a deoxynucleotide triphosphate solution containing 10 mM each of dATP, dGTP, dTTP and 5-methyl-dCTP (Pharmacia Biotech Inc., Piscataway, N.J.). The reaction mixture was incubated at 45° C. for 4 minutes followed by the addition of 10 µl of 200 U/µl of RNase H$^-$ reverse transcriptase (SUPERSCRIPT™ reverse transcriptase; GIBCO BRL) to the RNA-primer mixture. The reaction mixture was incubated at 45° C. for 1 hour followed by an incubation at 50° C. for 15 minutes. Sixty µl of TE (10 mM Tris-HCl, pH 8.0, 1 mM EDTA) was added to the reaction mixture, which was then fractionated by chromatography through a 400 pore size gel filtration column (CHROMA SPIN+TE-400™; Clontech Laboratories, Inc.) to remove excess primer.

First strand HEL cell cDNA was used as a template for the amplification of human MPL-P receptor cDNA using primers corresponding to the region encoding the amino and carboxyl termini of the receptor protein (Vigon et al., ibid.). The primers also each incorporated a different restriction enzyme cleavage site to aid in the directional cloning of the amplified product (ZC5746, SEQ ID NO:15, containing an Eco RI site; ZC5762, SEQ ID NO:16, containing an Xho I site). A 100 µl reaction was set up containing 10 ng of template cDNA, 50 pmoles of each primer; 200 µM of each deoxynucleotide triphosphate (Pharmacia Biotech, Inc.); 1 µl of 10× PCR buffer (Promega Corp.); and 10 units of Taq polymerase (Roche Molecular Systems, Inc., Branchburg, N.J.). The polymerase chain reaction was run for 35 cycles (1 minute at 95° C., 1 minute at 60° C. and 2 minutes at 72° C. with 1 extra second added to each successive cycle) followed by a 10 minute incubation at 72° C.

Human MPL-K receptor cDNA was isolated by polymerase chain reaction amplification from HEL cell cDNA in the manner described above, except primer ZC5762 (SEQ ID NO:16) was replaced with ZC5742 (SEQ ID NO:17). PCR primer ZC5742 was specific to the 3' terminus of human MPL-K cDNA and incorporated an Xho I restriction site to facilitate cloning.

The reaction products were extracted twice with phenol/chloroform (1:1), then once with chloroform and were ethanol precipitated. Following digestion with Eco RI and Xho I, the products were fractionated on a 0.8% low melt agarose gel (SEAPLAQUE GTG™ low melt agarose; FMC Corp., Rockland, Me.). A 1.9 kb amplified product corresponding to human MPL-P receptor cDNA and a 1.7 kb product corresponding to human MPL-K receptor cDNA were recovered from the excised gel slices by digestion of the gel matrix with β-agarase I (New England Biolabs, Inc., Beverly, Mass.) followed by ethanol precipitation. The cDNAs were subcloned into the vector pBluescript® SK+ (Stratagene Cloning Systems) for validation by sequencing.

Example 4
Cloning of Mouse MPL Receptor cDNAs

Spleens from C57BL/KsJ-db/db mice were removed and immediately placed in liquid nitrogen. Total RNA was prepared from spleen tissue using guanidine isothiocyanate (Chirgwin et al., *Biochemistry* 18: 52–94, 1979) followed by a CsCl centrifugation step. Spleen poly(A)+ RNA was isolated using oligo d(T) cellulose chromatography (Aviv and Leder, *Proc. Natl. Acad. Sci. U.S.A.* 69: 1408–1412, 1972).

Seven and a half µl of poly d(T)-selected poly(A)$^+$ mouse spleen RNA at a concentration of 1.7 µg/µl was mixed with 3 µl of 20 pmole/µl first strand primer ZC6091 (SEQ ID NO:18) containing a Not I restriction site. The mixture was heated at 65° C. for 4 minutes and cooled by chilling on ice. First strand cDNA synthesis was initiated by the addition of 8 µl of 250 mM Tris-HCl, pH 8.3, 375 mM KCl, 15 mM MgCl$_2$ (5× SUPERSCRIPT™ buffer; GIBCO BRL), 4 µl of 100 mM dithiothreitol and 3 µl of a deoxynucleotide triphosphate solution containing 10 mM each of dATP, dGTP, dTTP and 5-methyl-dCTP (Pharmacia Biotech Inc.) to the RNA-primer mixture. The reaction mixture was incubated at 45° C. for 4 minutes followed by the addition of 10 µl of 200 U/µl RNase H$^-$ reverse transcriptase (GIBCO BRL). The efficiency of the first strand synthesis was analyzed in a parallel reaction by the addition of 10 µCi of $^{32}$P-αdCTP to a 10 µl aliquot of the reaction mixture to label the reaction for analysis. The reactions were incubated at 45° C. for 1 hour followed by an incubation at 50° C. for 15 minutes. Unincorporated $^{32}$P-αdCTP in the labeled reaction was removed by chromatography on a 400 pore size gel filtration column (CHROMA SPIN+TE-400™; Clontech Laboratories Inc.). Unincorporated nucleotides in the unlabeled first strand reaction were removed by twice precipitating the cDNA in the presence of 8 µg of glycogen carrier, 2.5 M ammonium acetate and 2.5 volume ethanol. The unlabeled cDNA was resuspended in 50 µl water for use in second strand synthesis. The length of the labeled first strand cDNA was determined by agarose gel electrophoresis.

Second strand synthesis was performed on first strand cDNA under conditions that promoted first strand priming of second strand synthesis resulting in DNA hairpin formation. The reaction mixture was assembled at room temperature and consisted of 50 µl of the unlabeled first strand cDNA, 16.5 µl water, 20 µl of 5× polymerase I buffer (100 mM Tris-HCl, pH 7.4, 500 mM KCl, 25 mM MgCl$_2$, 50 mM (NH$_4$)$_2$SO$_4$), 1 µl of 100 mM dithiothreitol, 2 µl of a solution containing 10 mM of each deoxynucleotide triphosphate, 3 µl of 5 mM β-NAD, 15 µl of 3 U/µl *E. coli* DNA ligase (New England Biolabs Inc., Beverly, Mass.) and 5 µl of 10 U/µl *E. coli* DNA polymerase I (Amersham Corp., Arlington Heights, Ill.). The reaction was incubated at room temperature for 5 minutes followed by the addition of 1.5 µl of 2 U/µl RNase H (GIBCO BRL). A parallel reaction in which a 10 µl aliquot of the second strand synthesis mixture was labeled by the addition of 10 µCi $^{32}$P-αdCTP was used to monitor the efficiency of second strand synthesis. The reactions were incubated at 15° C. for two hours followed by a 15 minute incubation at room temperature. Unincorporated $^{32}$P-αdCTP in the labeled reaction was removed by chromatography through a 400 pore size gel filtration column (Clontech Laboratories, Inc.) before analysis by agarose gel electrophoresis. The unlabeled reaction was terminated by two extractions with phenol/chloroform and a chloroform extraction followed by ethanol precipitation in the presence of 2.5 M ammonium acetate.

The single-stranded DNA of the hairpin structure was cleaved using mung bean nuclease. The reaction mixture contained 100 µl of second strand cDNA, 20 µl of 10× mung bean nuclease buffer (Stratagene Cloning Systems, La Jolla, Calif.), 16 µl of 100 mM dithiothreitol, 51.5 µl of water and 12.5 µl of a 1:10 dilution of mung bean nuclease (Promega Corp.; final concentration 10.5 U/µl) in mung bean nuclease dilution buffer. The reaction was incubated at 37° C. for 15 minutes. The reaction was terminated by the addition of 20 µl of 1 M Tris-HCl, pH 8.0 followed by sequential phenol/chloroform and chloroform extractions as described above. Following the extractions, the DNA was precipitated in ethanol and resuspended in water.

The resuspended cDNA was blunt-ended with T4 DNA polymerase. The cDNA, which was resuspended in 190 µl of water, was mixed with 50 µl 5× T4 DNA polymerase buffer (250 mM Tris-HCl, pH 8.0, 250 mM KCl, 25 mM $MgCl_2$), 3 µl 0.1 M dithiothreitol, 3 µl of a solution containing 10 mM of each deoxynucleotide triphosphate and 4 µl of 1 U/µl T4 DNA polymerase (Boehringer Mannheim, Inc.). After an incubation of 1 hour at 10° C., the reaction was terminated by the addition of 10 µl of 0.5 M EDTA followed by serial phenol/chloroform and chloroform extractions as described above. The DNA was chromatographed through a 400 pore size gel filtration column (Clontech Laboratories, Inc.) to remove trace levels of protein and to remove short cDNAs less than ~400 bp in length. The DNA was ethanol precipitated in the presence of 12 µg glycogen carrier and 2.5 M ammonium acetate and was resuspended in 10 µl of water. Based on the incorporation of $^{32}$P-αdCTP, the yield of cDNA was estimated to be ~2 µg from a starting mRNA template of 12.5 µg.

Eco RI adapters were ligated onto the 5' ends of the cDNA to enable cloning into a lambda phage vector. A 10 µl aliquot of cDNA (~2 µg) and 10 µl of 65 pmole/µl Eco RI adapter (Pharmacia Biotech Inc.) were mixed with 2.5 µl 10× ligase buffer (Promega Corp.), 1 µl of 10 mM ATP and 2 µl of 15 U/µl T4 DNA ligase (Promega Corp.). The reaction was incubated overnight (~18 hours) at a temperature gradient of 0° C. to 18° C. The reaction was further incubated overnight at 12° C. The reaction was terminated by the addition of 75 µl of water and 10 µl of 3 M Na acetate, followed by incubation at 65° C. for 30 minutes. After incubation, the cDNA was extracted with phenol/chloroform and chloroform as described above and precipitated in the presence of 2.5 M ammonium acetate and 1.2 volume of isopropanol. Following centrifugation, the cDNA pellet was washed with 70% ethanol, air dried and resuspended in 89 µl water.

To facilitate the directional cloning of the cDNA into a lambda phage vector, the cDNA was digested with Not I, resulting in a cDNA having 5' Eco RI and 3' Not I cohesive ends. The Not I restriction site at the 3' end of the cDNA had been previously introduced through primer ZG6091 (SEQ ID NO:18). Restriction enzyme digestion was carried out in a reaction containing 89 µl of cDNA described above, 10 µl of 6 mM Tris-HCl, 6 mM $MgCl_2$, 150 mM NaCl, 1 mM DTT (10× D buffer; Promega Corp.) and 1 µl of 12 U/µl Not I (Promega Corp.). Digestion was carried out at 37° C. for 1 hour. The reaction was terminated by serial phenol/chloroform and chloroform extractions. The cDNA was ethanol precipitated, washed with 70% ethanol, air dried and resuspended in 20 µl of 1× gel loading buffer (10 mM Tris-HCl, pH 8.0, 1 mM EDTA, 5% glycerol and 0.125% bromphenol blue).

The resuspended cDNA was heated to 65° C. for 5 minutes, cooled on ice and electrophoresed on a 0.8% low melt agarose gel (SEA PLAQUE GTG™ low melt agarose; FMC Corp.). Unincorporated adapters and cDNA below 1.6 kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water (300 µl) approximately three times the volume of the gel slice was added to the tube, and the agarose was melted by heating to 65° C. for 15 minutes. Following equilibration of the sample to 42° C., 10 µl of 1 U/µl β-agarase I (New England Biolabs, Inc.) was added, and the mixture was incubated for 90 minutes to digest the agarose. After incubation, 40 µl of 3 M Na acetate was added to the sample, and the mixture was incubated on ice for 15 minutes. The sample was centrifuged at 14,000×g for 15 minutes at room temperature to remove undigested agarose. The cDNA in the supernatant was ethanol precipitated, washed in 70% ethanol, air-dried and resuspended in 37 µl of water for the kinase reaction to phosphorylate the ligated Eco RI adapters.

To the 37 µl cDNA solution described above was added 10 µl 10× ligase buffer (Stratagene Cloning Systems), and the mixture was heated to 65° C. for 5 minutes. The mixture was cooled on ice, and 5 µl 10 mM ATP and 3 µl of 10 U/µl T4 polynucleotide kinase (Stratagene Cloning Systems) were added. The reaction was incubated at 37° C. for 45 minutes and was terminated by heating to 65° C. for 10 minutes followed by serial extractions with phenol/chloroform and chloroform. The phosphorylated cDNA was ethanol precipitated in the presence of 2.5 M ammonium acetate, washed with 70% ethanol, air dried and resuspended in 12.5 µl water. The concentration of the phosphorylated cDNA was estimated to be ~40 fmole/µl.

The resulting cDNA was cloned into the lambda phage vector λExCell™ (Pharmacia Biotech Inc.), purchased predigested with Eco RI and Not I and dephosphorylated. Ligation of cDNA to vector was carried out in a reaction containing 2 µl of 20 fmole/µl prepared λExCell™ phage arms, 4 µl of water, 1 µl 10× ligase buffer (Promega Corp.), 2 µl of 40 fmole/µl cDNA and 1 µl of 15 U/µl T4 DNA ligase (Promega Corp.). Ligation was carried out at 4° C. for 48 hours. Approximately 50% of the ligation mixture was packaged into phage using GIGAPACK® II Gold packaging extract (Stratagene Cloning Systems) according to the directions of the vendor. The resulting cDNA library contained over 1.5×10$^7$ independent recombinants with background levels of insertless phage of less than 1.5%.

A $^{32}$P-labeled human MPL-K receptor cDNA probe was used to isolate mouse MPL receptor cDNA from the mouse spleen cDNA phage library. The cDNA library was plated on SURE® strain of E. coli cells (Stratagene Cloning Systems) at a density of 40,000 to 50,000 PFU/150 mm diameter plate. Phage plaques from thirty-three plates were transferred onto nylon membranes (Hybond N™; Amersham Corp., Arlington Heights, Ill.) and processed according to the directions of the manufacturer. The processed filters were baked for 2 hours at 80° C. in a vacuum oven followed by several washes at 70° C. in wash buffer (0.25× SSC, 0.25% SDS, 1 mM EDTA) and prehybridized overnight at 65° C. in hybridization solution (5× SSC, 5× Denhardt's solution, 0.1% SDS, 1 mM EDTA and 100 µg/ml heat denatured salmon sperm DNA) in a hybridization oven (model HB-2; Techne Inc., Princeton, N.J.). Following prehybridization, the hybridization solution was discarded and replaced with fresh hybridization solution containing approximately 2×10$^6$ cpm/ml of $^{32}$P-labeled human MPL-K cDNA prepared by the use of a commercially available labeling kit (MEGAPRIME™ kit; Amersham Corp., Arlington Heights, Ill.). The probe was denatured at 98° C. for 5 minutes before being added to the hybridization solution. Hybridization was carried out at 65° C. overnight. The filters were washed at 55° C. in wash buffer (0.25× SSC, 0.25%

SDS, 1 mM EDTA) and were autoradiographed with intensifying screens for 4 days at −70° C. on XAR-5 film (Eastman Kodak Co., Rochester, N.Y.). Employing the autoradiograph as template, agar plugs were recovered from regions of the plates corresponding to primary signals and were soaked in SM (0.1 M NaCl; 50 mM Tris-HCl, pH 7.5, 0.02% gelatin) to elute phage for plaque purification. Seven plaque-purified phages were isolated that carried inserts hybridizing to the human MPL-K receptor probe. The phagemids contained within the λExCell™ phage were recovered using the in vivo recombination system in accordance with the directions of the vendor. The identity of the cDNA inserts was confirmed by DNA sequencing.

The isolated clones encoded a protein exhibiting a high degree of sequence identity to human MPL-P receptor and to a recently reported mouse MPL receptor (Skoda et al., EMBO J. 12: 2645–2653, 1993). The seven clones fell into two classes differing from each other by three clones having a deletion of sequences encoding a stretch of 60 amino acid residues near the N-terminus. The cDNA encoding the protein without the deletion was referred to as mouse Type I MPL receptor cDNA. Type II receptor cDNA lacked sequences encoding Type I receptor residues 131 to 190 of SEQ ID NO: 7. In addition, Type I and II receptors differed from the reported mouse MPL receptor sequence (Skoda et al., ibid.) by the presence of a sequence encoding the amino acid residues Val-Arg-Thr-Ser-Pro-Ala-Gly-Glu (SEQ ID NO: 19) inserted after amino acid residue 222 and by a substitution of a glycine residue for serine at position 241 (positions refer to the Type I mouse receptor).

Type I and II mouse MPL receptor cDNAs were subcloned into the plasmid vector pHZ-1 for expression in mammalian cells. Plasmid pHZ-1 is an expression vector that may be used to express protein in mammalian cells or in a frog oocyte translation system from mRNAs that have been transcribed in vitro. The pHZ-1 expression unit comprises the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-1 contains an E. coli origin of replication; a bacterial beta lactamase gene; a mammalian selectable marker expression unit comprising the SV40 promoter and origin, a neomycin resistance gene and the SV40 transcription terminator. To facilitate directional cloning into pHZ-1, a polymerase chain reaction employing appropriate primers was used to create an Eco RI site and a Xho I site upstream from the translation initiation codon and downstream from the translation termination codon, respectively. The polymerase chain reaction was carried out in a mixture containing 10 µl 10× ULTMA™ DNA polymerase buffer (Roche Molecular Systems, Inc.), 6 µl of 25 mM MgCl$_2$, 0.2 µl of a deoxynucleotide triphosphate solution containing 10 mM each of dATP, dGTP, dTTP and dCTP (Pharmacia Biotech Inc.), 2.5 µl of 20 pmole/µl primer ZC6603 (SEQ ID NO: 20), 2.5 µl of 20 pmole/µl primer ZC5762 (SEQ ID NO: 16), 32.8 µl of water, 1 µl of an early log phase bacterial culture harboring either a Type I or a Type II mouse MPL receptor plasmid and 1 µl of 6 U/µl DNA polymerase (ULTMA™ polymerase; Roche Molecular Systems, Inc.). AmpliWaX™ (Roche Molecular Systems, Inc.) was employed in the reaction according to the directions of the vendor. The polymerase chain reaction was run for 25 cycles (1 minute at 95° C., 1 minute at 55° C. and 3 minutes at 72° C.) followed by a 10 minute incubation at 72° C. The amplified products were serially extracted with phenol/chloroform, then ethanol precipitated in the presence of 6 µg glycogen carrier and 2.5 M ammonium acetate. The pellets were resuspended in 87 µl of water to which was added 10 µl of 10×H buffer (Boehringer Mannheim, Inc.), 2 µl of 10 U/µl Eco RI (Boehringer Mannheim, Inc) and 1 µl of 40 U/µl Xho I (Boehringer Mannheim, Inc.). Digestion was carried out at 37° C. for 1 hour. The reaction was terminated by heating to 65° C. for 15 minutes and chromatographed through a 400 pore size gel filtration column (CHROMA SPIN+TE-400™; Clontech Laboratories Inc.).

The isolated receptor inserts described above were ligated into Eco RI and Xho I digested and dephosphorylated pHZ-1 vector. The ligation reaction contained 1 µl of 50 ng/µl prepared pHZ-1 vector, 5 µl of 5 ng/µl cDNA insert, 2 µl of 10× ligase buffer (Promega Corp.), 11.75 µl water and 0.25 µl of 4 U/µl T4 DNA ligase (Stratagene Cloning Systems). Ligation was carried out at 10° C. overnight. The ligated DNAs were transfected into E. coli (MAX EFFICIENCY DH10B™ competent cells; GIBCO BRL) in accordance with the vendor's directions. The validity of Type I and Type II mouse MPL and human MPL-P receptor inserts in pHZ-1 was confirmed by DNA sequencing. The resulting plasmids pSLmpl-8 and pSLmpl-9 carried the mouse Type II and Type I MPL receptor cDNAs, respectively. Plasmid pSLmpl-44 carried the human MPL-P cDNA insert.

Example 5
Preparation of Soluble MPL Receptor

A mammalian expression plasmid encoding soluble mouse Type I MPL receptor (pLDmpl-53) was produced by combining DNA segments from pSLmpl-9, a mammalian expression plasmid containing the cDNA encoding full-length mouse Type I MPL receptor described above, with a DNA segment from pSLmpl-26, an expression plasmid constructed to produce the soluble mouse Type I MPL receptor in bacteria.

A cDNA segment encoding mouse Type I MPL soluble receptor was isolated by PCR employing primers ZC6704 (SEQ ID NO: 21) and ZC6703 (SEQ ID NO: 22) using full-length receptor plasmid pSLmpl-9 as template. To facilitate directional cloning, primers ZC6704 and ZC6703 incorporated Eco RI and Xho I restriction sites at their respective 5' ends. Primer ZC6703 also encoded an inframe consensus target sequence for protein kinase to enable in vitro labeling of the purified soluble receptor with $^{32}$P γ-ATP (Li et al., Proc. Natl. Acad. Sci. U.S.A. 86: 558–562, 1989). The PCR was carried out in a mixture containing 10 µl 10× ULTMA™ DNA polymerase buffer (Roche Molecular Systems, Inc.), 6 µl of 25 mM MgCl$_2$, 0.2 µl of a deoxynucleotide triphosphate solution containing 10 mM each of dATP, dGTP, dTTP and dCTP (Pharmacia Biotech Inc.), 11 µl of 4.55 pmole/µl primer ZC6704 (SEQ ID NO: 21), 21 µl of 2.43 pmole/µl primer ZC6703 (SEQ ID NO: 22), 50.3 µl of water, 1 µl 50 ng/µl Hind III and Xba I digested pSLmpl-9 and 1 µl of 6 U/µl ULTMA™ DNA polymerase (Roche Molecular Systems, Inc.). AmpliWax™ (Roche Molecular Systems, Inc.) was employed in the reaction according to the directions of the vendor. The polymerase chain reaction was run for 3 cycles (1 minute at 95° C., 1 minute at 50° C. and 2 minutes at 72° C.) followed by 11 cycles at increased hybridization stringency (1 minute at 95° C., 30 seconds at 55° C. and 2 minutes at 72° C.) followed by a 10 minute incubation at 72° C. The amplified product was serially extracted with phenol/chloroform and chloroform followed by chromatography through a 400 pore size gel filtration column (Clontech Laboratories, Inc.). The PCR product was ethanol precipitated in the presence of 20 µg glycogen carrier and 2.5 M ammonium acetate. The pellet was resuspended in 32 μl of water. To 16 μl of the resuspended PCR product was added 2 μl 10× H buffer (Boehringer Mannheim, Inc.), 1 μl of 10 U/μl Eco RI (Boehringer Mannheim, Inc.) and 1 μl of 40 U/μl Xho I (Boehringer Mannheim, Inc.). Digestion was carried out at 37° C. for 1 hour. Digestion was terminated by heating to 65° C. for 15 minutes, and DNA was purified on a 0.7% low-melt agarose gel. Fragment recovery from low-melt agarose was done by digestion of the gel matrix with β-agarase I (New England Biolabs).

The resulting PCR product encoded the N-terminal extracellular domain of mouse Type I MPL receptor (residues 27 to 480 of SEQ ID NO: 7). In the absence of the putative receptor trans-membrane domain (residues 483 to 504 of SEQ ID NO: 7) the expressed protein is expected to be secreted in the presence of a suitable signal peptide. A mouse Type II soluble MPL receptor cDNA was obtained using the PCR conditions described above except that pSLmpl-8 was used as template. The validity of both receptor fragments was confirmed by DNA sequencing.

The soluble mouse Type I and Type II MPL receptor DNA fragments were cloned into Eco RI and Xho I digested vector pOmpA2-5 to yield pSLmpl-26 and pSLmpl-27, respectively. Plasmid pOmpA2-5 is a modification of pOmpA2 (Ghrayab et al., *EMBO J.* 3: 2437–2442, 1984), a bacterial expression vector designed to target the recombinant protein to the periplasmic space. pOmpA2-5 was constructed by replacement of a 13 bp sequence between the Eco RI and Bam HI sites of pOmpA2 with a synthetic 42 bp sequence. The sequence was created by annealing of two 42 nucleotide complementary oligonucleotides (ZC6707, SEQ ID NO: 23; ZC 6706, SEQ ID NO: 24), which when base paired formed Eco RI and Bam HI cohesive ends, facilitating directional cloning into Eco RI and Bam HI digested pOmpA2. Within the inserted sequence is an Xho I site inframed with respect to a bacterial leader sequence and to the mouse MPL soluble receptor cDNAs described above, as well as an inframe tract of 6 histidine codons located 3' of the Xho I site to enable the recombinant protein to be purified by metal chelation affinity chromatography (Houchuli et al., *Bio/Technol.* 6: 1321–1325, 1988). Following the sequence encoding the histidine tract was an inframe termination codon. The validity of the pOmpA2-5, pSLmpl-26 and pSLmpl-27 was confirmed by DNA sequencing.

pLDmpl-53, a mammalian expression plasmid producing soluble mouse Type I MPL receptor polypeptide, was constructed by combining DNA segments from pSLmpl-9 and pSLmpl-26 into expression vector pHZ-200 (pHZ-1 in which a dihydrofolate reductase sequence was substituted for the neomycin resistance gene). The 1164 bp Eco RI/Bam HI cDNA fragment from pSLmpl-9 replaced the mammalian signal sequence deleted during the construction of bacterial expression plasmid pSLmpl-26. The 416 bp Bam HI fragment from pSLmpl-26 supplied the coding sequence for the carboxy-terminal portion of the soluble MPL receptor, the kinase labeling domain, the poly-histidine tract and the translation terminator. The two fragments were gel purified and cloned into the Eco RI/Bam HI sites of pBluescript® KS+ (Stratagene Cloning Systems) to yield plasmid pBS8.76LD-5. Correct orientation of the 416 bp pSLmpl-26 derived Bam HI fragment with respect to the 1164 bp pSLmpl-9 derived Eco RI/Bam HI fragment in pBS8.76LD-5 was determined by PCR using primers ZC 6603 (SEQ ID NO: 20) and ZC 6703 (SEQ ID NO: 22). The Xba I site within the poly-linker sequence of pBS8.76LD-5 enabled the reconstituted receptor cDNA to be excised as a 1.5 kb Eco RI/Xba I fragment for cloning into pHZ-200 following digestion of the vector with Eco RI and Xba I. The resulting mammalian expression plasmid, pLDmpl-53, was prepared in large scale for transfection into BHK cells.

Twenty micrograms of purified pLDmpl-53 plasmid was transfected into BHK 570 cells using the calcium phosphate precipitation method. After 5 hours, the cells were shocked with 15% glycerol for 3 minutes to facilitate uptake of DNA. Fresh growth media was added overnight. The following day the cells were split at various dilutions, and selection media containing 1 μM methotrexate was added. After approximately two weeks, discrete, methotrexate-resistant colonies were visible. Resistant colonies were either pooled or maintained as distinct clones. Spent media from the pooled colonies was immediately tested for presence of soluble MPL receptor polypeptide.

Soluble MPL receptor polypeptide was isolated through the interaction of the poly-histidine tract present on the carboxy-terminus of the polypeptide with a metal chelation resin containing immobilized $Ni^{2+}$ (HIS-BIND™; Novagen, Madison, Wis.). Serum-free spent culture media from the pLDmpl-53 pool was passed over the resin, and bound polypeptide was eluted with 1 M imidazole. SDS-PAGE analysis revealed a single band at ~67 kDa. This polypeptide was subjected to N-terminal amino acid analysis and confirmed to be mouse MPL receptor.

Soluble mouse MPL receptor polypeptide was purified from a pool of BHK transfectants, which had been transfected with the plasmid pLDmpl-53. The purified soluble receptor polypeptide was immobilized on CNBr-activated SEPHAROSE™ 4B (Pharmacia Biotech) matrix essentially as directed by the manufacturer and used for affinity purification of the MPL activity in conditioned media of 24-11-5 cells. The affinity matrix was packed in a XK16 column (Pharmacia Biotech). Conditioned media from 24-11-5 cells were concentrated on a 10 kD cut off hollow fiber membrane (A/G Technology Corp., Needham, Mass.) and loaded onto the bottom of the MPL receptor affinity column at a flow rate of 1 ml/minute. The column was washed with phosphate buffed saline (PBS) containing 0.5 M NaCl and 0.01% sodium azide. MPL activity (thrombopoietin) was eluted from the column with 3 M potassium thiocyanate (Sigma Chemical Company, St. Louis, Mo.) at a flow rate of 0.5 ml/minute. Potassium thiocyanate was removed by dialysis against PBS.

Active fractions from the affinity column were identified using a colorimetric assay based on the metabolic breakdown of 3-(4,5-dimethylthiazol-2-yl)-2,5-diphenyl tetrazolium bromide (MTT) (Mosman, *J. Immunol. Meth.* 65: 55–63, 1983). Twenty μl of a 10 mg/ml solution of MTT (Polyscience, Inc., Warrington, Pa.) was added to 100 μl of BaF3/MPLR1.1 assay cells, and the cells were incubated at 37° C. After 4 hours, 200 μl of 0.04 N HCl in isopropanol was added, the solution was mixed, and the absorbance of the sample was read at 570 nm on a model EL320 ELISA reader (Bio-Tek Instruments Inc., Highland Park, Vt.).

Example 6

Preparation of Recombinant Human TPO

Plasmid DNA from two 5 ml overnight bacterial cultures transformed with pZGmpl-124 was prepared by alkaline cell lysis followed by binding of DNA to a resin at high salt (using a Magic Minipreps™ Sampler kit from Promega Corp.). The DNA was eluted with 75 μl 10 mM Tris, 1 mM EDTA, pH 8.0.

BHK 570 cell cultures at 50,000 cells/well were transfected with pZGmpl-124 DNA. 20 μl of a 1:10 dilution of LIPOFECTAMINE™ (GIBCO BRL) was added to 20 μl of plasmid DNA and 160 μl of serum free media (F/DV media

[a 1:1 mixture of DMEM and Ham's F12] supplemented with 10 μg/ml fetuin, 2 ng/ml selenium, 5 μg/ml insulin, 10 μg/ml transferin, 2 mM L-glutamine, 110 μg/ml sodium pyruvate, 25 mM HEPES, and 0.1 mM non-essential amino acid solution (GIBCO BRL)) for 30 minutes at room temperature before adding to BHK 570 cells and incubating for 4 hours at 37° C. 200 μl of Growth Media (DMEM (BioWhittaker, Inc., Walkersville, Md.) supplemented with 2 mM L-glutamine, 110 μg/ml sodium pyruvate, 0.05 mg/ml penicillin, 0.05 mg/ml streptomycin, 0.01 mg/ml neomycin, 25 mM HEPES, 10% fetal calf serum) was then added, and the cells were incubated at 37° C. overnight. The culture media was then replaced with Growth Medium containing 5% fetal calf serum, and the cells were incubated at 37° C. for 4 hours.

The conditioned media from the BHK 570 transfectants were then assayed for the ability to cause cell proliferation in BaF3 cells expressing the mouse MPL receptor. The cells were grown in BaF3 media (RPMI 1640 media (JRH Biosciences, Lexena, Kans.) supplemented with 10% fetal calf serum, 2mM L-glutamine, lmM sodium pyruvate, 10 mM HEPES, 57 μM β-Mercaptoethanol, 0.05 mg/ml penicillin, 0.05 mg/ml streptomycin, 0.01 mg/ml neomycin and 4% V/V conditioned medium from cultures of WEHI-3 cells (mouse interleukin-3, culture supplement, Collaborative Biomedical Products)). Prior to assay, BaF3 cells were diluted and resuspended in IL-3-free BaF3 medium to 10,000 cells/100 1μl. 100 μl of conditioned medium from pZGmpl-124 transfected BHK 570 cells was added, and the cultures were incubated at 37° C. Cells were then visually examined for cell elongation after 30 minutes and after 24 hours. A negative control consisting of BaF3 medium without IL-3 and a positive control of conditioned medium from BHK 570 cells transfected with the mouse TPO DNA were also assayed. Results showed no cell elongation of BaF3 cells in the negative control, some cell elongation in the positive control and significant cell elongation in the pZGmpl-124 transfected cells.

Example 7
Preparation of Recombinant Mouse TPO

Plasmid pZGmpl-1081 was digested with Eco RI and Not I, and the TPO DNA segment was recovered. This DNA was inserted into Eco RI-digested, alkaline phosphatase-treated plasmid Zem229R with a Not I/Eco RI linker. The resulting plasmid, designated mpl.229R, was transfected into BHK 570 cells (ATCC CRL 10314). The transfectants were grown in 10-layer cell factories (Nunc, Inc.; obtained from VWR Scientific, Seattle, WA) in serum-free medium and selected in 1 μM methotrexate. Sixteen liters of conditioned culture medium was collected.

Example 8
Purification and Characterization of TPO

Human and mouse TPO were purified from conditioned cell culture media by a combination of ultrafiltration, affinity chromatography on immobilized MPL receptor, and anion exchange chromatography.

Forty to sixty liters of crude conditioned culture medium was concentrated on a 10,000 molecular weight cutoff membrane to approximately one liter. The concentrate was adjusted to 0.5 M NaCl by addition of 4.0 M NaCl, and the pH was adjusted to pH 8.5. The solution was then passed through a 0.22μ filter and applied to a 2.5 cm (diameter) by 4.0 cm (height) column of soluble mouse MPL receptor bound to CNBr-activated Sepharose™ (Pharmacia Biotech) (approximately 15 mg of receptor per ml of swollen resin). The flow rate of application was 5.0 ml/minute, and the column was run at 4° C. After sample application the column was washed with 100 ml of 20 mM Tris, pH 8.5 containing 0.5 M NaCl. TPO was eluted from the column with 20 mM Tris, pH 9.5, 3.0 M KSCN at a flow rate of 5.0 ml/minute. Protein elution was monitored by absorbence at 280 nm. Fractions containing protein eluate were dialyzed in 20 mM Tris, pH 8.5 to remove KSCN. Dialyzed eluate was then applied to a Mono Q® HR5/5 column (Pharmacia Biotech) at a flow rate of 2.0 ml/minute, and the column was run at 20° C. After sample application, the column was washed with 20 ml of 20 mM Tris, pH 8.5. Protein was then eluted with a 20 minute gradient from 0 to 0.5 M NaCl in 20 mM Tris, pH 8.5. The elution, profile was monitored by absorbence at 220 nm, and 2.0 ml fractions were collected.

Western blotting was used in conjunction with sodium dodecyl sulphate-polyacrylamide gel electrophoresis (SDS-PAGE) for visualization of column fractions. For mouse TPO, western blot analysis was done using rat polyclonal antisera produced against a peptide sequence derived from mouse TPO (Asp-52 to Leu-66 of SEQ ID NO: 2). Twenty μl of each fraction was electrophoresed on a 4–20% Tris-glycine SDS polyacrylamide gel in denaturing (reducing) sample buffer. Proteins were transferred to nitrocellulose by electroblotting. Proteins were visualized by reacting the blots with the rat anti-TPO peptide antisera followed by rabbit anti-rat antibody/horseradish peroxidase conjugate (BioSource International, Camarillo, Calif.) and ECLTm detection reagents (Amersham Corp.). The blots were then exposed to autoradiography film for either one or ten seconds as a means of determining relative amounts of 70 kD and ≧35 kD TPO species in the various fractions. If the ≧35 kD fragment bands were much less intense after 10 seconds exposure than the 70 kD fragment bands in the same lane after 1-second exposure, the fraction was determined to contain at least 90% 70 kD TPO. By visual inspection, some fractions were judged to be >95% 70 kD TPO. Fractions >90% 70 kD TPO were pooled. If the 70 kD band was less intense after a 10-second exposure than was the 35 kD band after a 1-second exposure in the same lane, the fraction was determined to contain at least 90% 35 kD TPO, and such fractions were also pooled. Ten μl (0.83 μg of 70 kD TPO and 0.24 μg of 35 kD TPO as determined by amino acid composition analysis) of pooled fractions was analyzed by SDS-PAGE (4–20% gel) under denaturing conditions followed by silver staining using a Daiichi silver stain kit (Catalog No. SE140001; Integrated Separation Systems, Natick, Mass.) according to the supplier's instructions. After development of the gel with silver stain, the 70 kD pooled fractions were determined to be essentially free of 35 kD TPO as judged by visual inspection of the gel lane, and the 35 kD fractions were judged to be essentially free of 70 kD material. A western blot showing fractionation of mouse TPO into 70 kD and lower molecular weight species is illustrated in FIG. 1.

Figure 2:
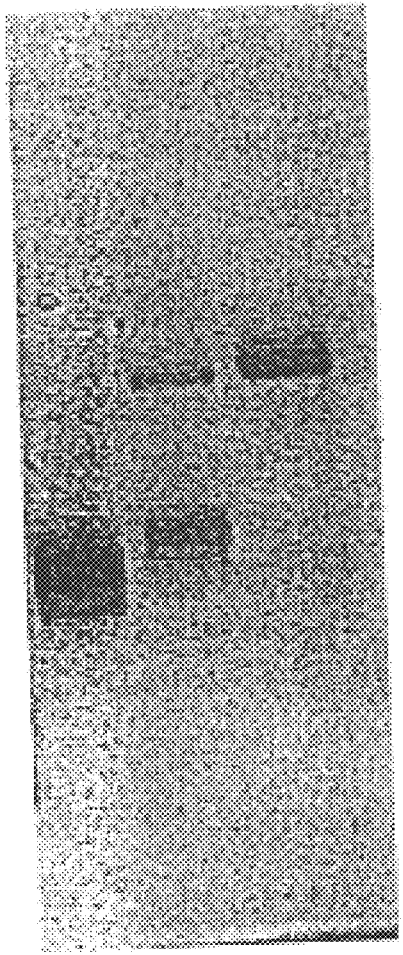
FIG. 2 illustrates fractionated human TPO electrophoresed on an SDS-polyacrylamide gel and silver stained.

Purified human TPO was analyzed by similar methods. Western blot analysis was carried out using rabbit polyclonal antisera to intact human TPO. Purity of human TPO fractions was similar to that observed for the mouse protein. FIG. 2 shows a silver stained gel of pooled human TPO fractions. The 70 kD fraction was judged to be >90% pure and essentially free of TPO species of $M_r$<55 kD.

Purified 70 kD TPO was assayed for biological activity by an in vitro mitogenesis assay on BaF3/MPLR1.1 cells (IL-3-dependent cells expressing a stably transfected Type I mouse MPL receptor; deposited on Sep. 28, 1994 under the terms of the Budapest Treaty with American Type Culture Collection, 12301 Parklawn Drive, Rockville, Md. and assigned accession number CRL 11723). The point of ½ maximal activity (average of 16 curves) was assigned the value of 50 U/ml. The original standard solution (serum-free medium conditioned by a BHK cell line transfected with pZGmpl-1081) was calculated to contain 26,600 U/ml mouse TPO. TPO samples were diluted in RPMI 1640 medium supplemented with 57 μM 2-mercaptoethanol, 2 mM L-glutamine, 1 mM sodium pyruvate, PSN antibiotic mixture, 10 mM HEPES and 10% heat inactivated fetal bovine serum, generally using 8–24 dilutions. Briefly, 100 μl of diluted test sample or standard sample and 100 μl BaF3 cells (final cell number added about 10,000 cells/well) were combined in wells of a 96 well plate. Internal standards included eight 2-fold dilutions of 100 U/ml mouse TPO for mouse TPO assays, or eight 2-fold dilutions of 150 U/ml mouse TPO for human TPO assays. To each well was added 2 μl $^3$H-thymidine (1 μCi/μl; Amersham), and the plates were incubated overnight at 37° C. The contents of each well of each plate were transferred to a filter/plate using a Packard apparatus. The filters were washed 8 times with water, and the filters were dried and counted. Units of TPO activity in each sample well were determined by comparison to the standard curve. Total protein content was determined by amino acid composition analysis. Purified 70 kD mouse TPO was found to have a specific activity of 129,000 units/μg, and purified 70 kD human TPO had a specific activity of 5,000 units/μg by these methods.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for purifying thrombopoietin from a biological fluid comprising:

applying a biological fluid containing thrombopoietin to a polypeptide comprising a ligand-binding domain of an MPL receptor, which polypeptide is bound to a solid support, whereby said thrombopoietin is adsorbed to said polypeptide;

washing the polypeptide to elute unadsorbed material;

eluting the adsorbed thrombopoietin from said polypeptide;

fractionating the eluted thrombopoietin by anion exchange chromatography; and collecting the fractionated thrombopoietin, wherein the collected thrombopoietin is characterized by:

a) $M_r$=70,000±10,000 daltons as determined by SDS-polyacrylamide gel electrophoresis under denaturing conditions;

b) at least 90% pure with respect to contaminating proteins as determined by SDS-polyacrylamide gel electrophoresis and silver staining;

c) essentially free of TPO species of $M_r$<55 kD; and d) stimulates MPL-dependent cell proliferation.

2. A method according to claim 1 wherein the biological fluid is conditioned cell culture media or milk.

3. A method according to claim 1 wherein the biological fluid is concentrated, conditioned cell culture media.

4. A method according to claim 1 further comprising the step of concentrating the biological fluid before applying it to the receptor polypeptide.

5. A method according to claim 1 wherein the solid support is cross-linked agarose beads.

6. A method according to claim 1 wherein the thrombopoietin is mouse thrombopoietin.

7. A method according to claim 1 wherein the thrombopoietin is primate thrombopoietin.

8. A method according to claim 1 wherein the thrombopoietin is human thrombopoietin.

9. A method according to claim 1 wherein the polypeptide comprises a ligand-binding domain of a mouse or human MPL receptor.

10. A method according to claim 9 wherein the polypeptide consists essentially of residues 27–480 of SEQ ID NO:7.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 1486 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 105..1241

(xi) SEQUENCE DESCRIPTION: SEQ ID NO:1:

```
CCTCGTGCCG GTCCTGAGGC CCTTCTCCAC CCGGACAGAG TCCTTGGCCC ACCTCTCTCC            60

CACCCGACTC TGCCGAAAGA AGCACAGAAG CTCAAGCCGC CTCC ATG GCC CCA GGA           116
                                                Met Ala Pro Gly
                                                  1

AAG ATT CAG GGG AGA GGC CCC ATA CAG GGA GCC ACT TCA GTT AGA CAC            164
Lys Ile Gln Gly Arg Gly Pro Ile Gln Gly Ala Thr Ser Val Arg His
  5                  10                  15                  20

CTG GCC AGA ATG GAG CTG ACT GAT TTG CTC CTG GCG GCC ATG CTT CTT            212
Leu Ala Arg Met Glu Leu Thr Asp Leu Leu Leu Ala Ala Met Leu Leu
                 25                  30                  35

GCA GTG GCA AGA CTA ACT CTG TCC AGC CCC GTA GCT CCT GCC TGT GAC            260
Ala Val Ala Arg Leu Thr Leu Ser Ser Pro Val Ala Pro Ala Cys Asp
             40                  45                  50

CCC AGA CTC CTA AAT AAA CTG CTG CGT GAC TCC CAC CTC CTT CAC AGC            308
Pro Arg Leu Leu Asn Lys Leu Leu Arg Asp Ser His Leu Leu His Ser
         55                  60                  65

CGA CTG AGT CAG TGT CCC GAC GTC GAC CCT TTG TCT ATC CCT GTT CTG            356
Arg Leu Ser Gln Cys Pro Asp Val Asp Pro Leu Ser Ile Pro Val Leu
     70                  75                  80

CTG CCT GCT GTG GAC TTT AGC CTG GGA GAA TGG AAA ACC CAG ACG GAA            404
Leu Pro Ala Val Asp Phe Ser Leu Gly Glu Trp Lys Thr Gln Thr Glu
 85                  90                  95                 100

CAG AGC AAG GCA CAG GAC ATT CTA GGG GCA GTG TCC CTT CTA CTG GAG            452
Gln Ser Lys Ala Gln Asp Ile Leu Gly Ala Val Ser Leu Leu Leu Glu
                105                 110                 115
```

-continued

```
GGA GTG ATG GCA GCA CGA GGA CAG TTG GAA CCC TCC TGC CTC TCA TCC        500
Gly Val Met Ala Ala Arg Gly Gln Leu Glu Pro Ser Cys Leu Ser Ser
            120                 125                 130

CTC CTG GGA CAG CTT TCT GGG CAG GTT CGC CTC CTC TTG GGG GCC CTG        548
Leu Leu Gly Gln Leu Ser Gly Gln Val Arg Leu Leu Leu Gly Ala Leu
        135                 140                 145

CAG GGC CTC CTA GGA ACC CAG CTT CCT CTA CAG GGC AGG ACC ACA GCT        596
Gln Gly Leu Leu Gly Thr Gln Leu Pro Leu Gln Gly Arg Thr Thr Ala
    150                 155                 160

CAC AAG GAC CCC AAT GCC CTC TTC TTG AGC TTG CAA CAA CTG CTT CGG        644
His Lys Asp Pro Asn Ala Leu Phe Leu Ser Leu Gln Gln Leu Leu Arg
165                 170                 175                 180

GGA AAG GTG CGC TTC CTG CTT CTG GTA GAA GGT CCC ACC CTC TGT GTC        692
Gly Lys Val Arg Phe Leu Leu Leu Val Glu Gly Pro Thr Leu Cys Val
                185                 190                 195

AGA CGG ACC CTG CCA ACC ACA GCT GTC CCA AGC AGT ACT TCT CAA CTC        740
Arg Arg Thr Leu Pro Thr Thr Ala Val Pro Ser Ser Thr Ser Gln Leu
            200                 205                 210

CTC ACA CTA AAC AAG TTC CCA AAC AGG ACT TCT GGA TTG TTG GAG ACG        788
Leu Thr Leu Asn Lys Phe Pro Asn Arg Thr Ser Gly Leu Leu Glu Thr
        215                 220                 225

AAC TTC AGT GTC ACA GCC AGA ACT GCT GGC CCT GGA CTT CTG AGC AGG        836
Asn Phe Ser Val Thr Ala Arg Thr Ala Gly Pro Gly Leu Leu Ser Arg
    230                 235                 240

CTT CAG GGA TTC AGA GTC AAG ATT ACT CCT GGT CAG CTA AAT CAA ACC        884
Leu Gln Gly Phe Arg Val Lys Ile Thr Pro Gly Gln Leu Asn Gln Thr
245                 250                 255                 260

TCC AGG TCC CCA GTC CAA ATC TCT GGA TAC CTG AAC AGG ACA CAC GGA        932
Ser Arg Ser Pro Val Gln Ile Ser Gly Tyr Leu Asn Arg Thr His Gly
                265                 270                 275

CCT GTG AAT GGA ACT CAT GGG CTC TTT GCT GGA ACC TCA CTT CAG ACC        980
Pro Val Asn Gly Thr His Gly Leu Phe Ala Gly Thr Ser Leu Gln Thr
            280                 285                 290

CTG GAA GCC TCA GAC ATC TCG CCC GGA GCT TTC AAC AAA GGC TCC CTG       1028
Leu Glu Ala Ser Asp Ile Ser Pro Gly Ala Phe Asn Lys Gly Ser Leu
        295                 300                 305

GCA TTC AAC CTC CAG GGT GGA CTT CCT CCT TCT CCA AGC TTG GCT CCT       1076
Ala Phe Asn Leu Gln Gly Gly Leu Pro Pro Ser Pro Ser Leu Ala Pro
    310                 315                 320

GAT GGA CAC ACA CCC TTC CCT CCT TCA CCT GCC TTG CCC ACC ACC CAT       1124
Asp Gly His Thr Pro Phe Pro Pro Ser Pro Ala Leu Pro Thr Thr His
325                 330                 335                 340

GGA TCT CCA CCC CAG CTC CAC CCC CTG TTT CCT GAC CCT TCC ACC ACC       1172
Gly Ser Pro Pro Gln Leu His Pro Leu Phe Pro Asp Pro Ser Thr Thr
                345                 350                 355

ATG CCT AAC TCT ACC GCC CCT CAT CCA GTC ACA ATG TAC CCT CAT CCC       1220
Met Pro Asn Ser Thr Ala Pro His Pro Val Thr Met Tyr Pro His Pro
            360                 365                 370

AGG AAT TTG TCT CAG GAA ACA TAGCGCGGGC ACTGGCCCAG TGAGCGTCTG          1271
Arg Asn Leu Ser Gln Glu Thr
        375

CAGCTTCTCT CGGGGACAAG CTTCCCCAGG AAGGCTGAGA GGCAGCTGCA TCTGCTCCAG     1331

ATGTTCTGCT TTCACCTAAA AGGCCCTGGG GAAGGGATAC ACAGCACTGG AGATTGTAAA     1391

ATTTTAGGAG CTATTTTTTT TTAACCTATC AGCAATATTC ATCAGAGCAG CTAGCGATCT     1451

TTGGTCTATT TTCGGTATAA ATTTGAAAAT CACTA                                1486
```

(2) INFORMATION FOR SEQ ID NO:2:

(i) SEQUENCE CHARACTERISTICS:

(A) LENGTH: 379 amino acids
            (B) TYPE: amino acid
            (D) TOPOLOGY: linear (ii) MOLECULE TYPE: protein (xi) SEQUENCE DESCRIPTION: SEQ ID NO:2:

Met Ala Pro Gly Lys Ile Gln Gly Arg Gly Pro Ile Gln Gly Ala Thr
 1               5                  10                  15

Ser Val Arg His Leu Ala Arg Met Glu Leu Thr Asp Leu Leu Leu Ala
                20                  25                  30

Ala Met Leu Leu Ala Val Ala Arg Leu Thr Leu Ser Ser Pro Val Ala
            35                  40                  45

Pro Ala Cys Asp Pro Arg Leu Leu Asn Lys Leu Leu Arg Asp Ser His
    50                  55                  60

Leu His Ser Arg Leu Ser Gln Cys Pro Asp Val Asp Pro Leu Ser
65              70                  75                  80

Ile Pro Val Leu Leu Pro Ala Val Asp Phe Ser Leu Gly Glu Trp Lys
                85                  90                  95

Thr Gln Thr Glu Gln Ser Lys Ala Gln Asp Ile Leu Gly Ala Val Ser
                100                 105                 110

Leu Leu Leu Glu Gly Val Met Ala Ala Arg Gly Gln Leu Glu Pro Ser
            115                 120                 125

Cys Leu Ser Ser Leu Leu Gly Gln Leu Ser Gly Gln Val Arg Leu Leu
    130                 135                 140

Leu Gly Ala Leu Gln Gly Leu Leu Gly Thr Gln Leu Pro Leu Gln Gly
145                 150                 155                 160

Arg Thr Thr Ala His Lys Asp Pro Asn Ala Leu Phe Leu Ser Leu Gln
                165                 170                 175

Gln Leu Leu Arg Gly Lys Val Arg Phe Leu Leu Leu Val Glu Gly Pro
            180                 185                 190

Thr Leu Cys Val Arg Arg Thr Leu Pro Thr Thr Ala Val Pro Ser Ser
        195                 200                 205

Thr Ser Gln Leu Leu Thr Leu Asn Lys Phe Pro Asn Arg Thr Ser Gly
210                 215                 220

Leu Leu Glu Thr Asn Phe Ser Val Thr Ala Arg Thr Ala Gly Pro Gly
225                 230                 235                 240

Leu Leu Ser Arg Leu Gln Gly Phe Arg Val Lys Ile Thr Pro Gly Gln
                245                 250                 255

Leu Asn Gln Thr Ser Arg Ser Pro Val Gln Ile Ser Gly Tyr Leu Asn
            260                 265                 270

Arg Thr His Gly Pro Val Asn Gly Thr His Gly Leu Phe Ala Gly Thr
        275                 280                 285

Ser Leu Gln Thr Leu Glu Ala Ser Asp Ile Ser Pro Gly Ala Phe Asn
290                 295                 300

Lys Gly Ser Leu Ala Phe Asn Leu Gln Gly Gly Leu Pro Pro Ser Pro
305                 310                 315                 320

Ser Leu Ala Pro Asp Gly His Thr Pro Phe Pro Pro Ser Pro Ala Leu
                325                 330                 335

Pro Thr Thr His Gly Ser Pro Pro Gln Leu His Pro Leu Phe Pro Asp
            340                 345                 350

Pro Ser Thr Thr Met Pro Asn Ser Thr Ala Pro His Pro Val Thr Met
        355                 360                 365

Tyr Pro His Pro Arg Asn Leu Ser Gln Glu Thr
370                 375

(2) INFORMATION FOR SEQ ID NO:3:

(i) SEQUENCE CHARACTERISTICS:
        (A) LENGTH: 1062 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1059

(xi) SEQUENCE DESCRIPTION: SEQ ID NO:3:

```
ATG GAG CTG ACT GAA TTG CTC CTC GTG GTC ATG CTT CTC CTA ACT GCA       48
Met Glu Leu Thr Glu Leu Leu Leu Val Val Met Leu Leu Leu Thr Ala
 1               5                  10                  15

AGG CTA ACG CTG TCC AGC CCG GCT CCT CCT GCT TGT GAC CTC CGA GTC       96
Arg Leu Thr Leu Ser Ser Pro Ala Pro Pro Ala Cys Asp Leu Arg Val
            20                  25                  30

CTC AGT AAA CTG CTT CGT GAC TCC CAT GTC CTT CAC AGC AGA CTG AGC      144
Leu Ser Lys Leu Leu Arg Asp Ser His Val Leu His Ser Arg Leu Ser
        35                  40                  45

CAG TGC CCA GAG GTT CAC CCT TTG CCT ACA CCT GTC CTG CTG CCT GCT      192
Gln Cys Pro Glu Val His Pro Leu Pro Thr Pro Val Leu Leu Pro Ala
 50                  55                  60

GTG GAC TTT AGC TTG GGA GAA TGG AAA ACC CAG ATG GAG GAG ACC AAG      240
Val Asp Phe Ser Leu Gly Glu Trp Lys Thr Gln Met Glu Glu Thr Lys
 65                  70                  75                  80

GCA CAG GAC ATT CTG GGA GCA GTG ACC CTT CTG CTG GAG GGA GTG ATG      288
Ala Gln Asp Ile Leu Gly Ala Val Thr Leu Leu Leu Glu Gly Val Met
                 85                  90                  95

GCA GCA CGG GGA CAA CTG GGA CCC ACT TGC CTC TCA TCC CTC CTG GGG      336
Ala Ala Arg Gly Gln Leu Gly Pro Thr Cys Leu Ser Ser Leu Leu Gly
            100                 105                 110

CAG CTT TCT GGA CAG GTC CGT CTC CTC CTT GGG GCC CTG CAG AGC CTC      384
Gln Leu Ser Gly Gln Val Arg Leu Leu Leu Gly Ala Leu Gln Ser Leu
        115                 120                 125

CTT GGA ACC CAG CTT CCT CCA CAG GGC AGG ACC ACA GCT CAC AAG GAT      432
Leu Gly Thr Gln Leu Pro Pro Gln Gly Arg Thr Thr Ala His Lys Asp
130                 135                 140

CCC AAT GCC ATC TTC CTG AGC TTC CAA CAC CTG CTC CGA GGA AAG GTG      480
Pro Asn Ala Ile Phe Leu Ser Phe Gln His Leu Leu Arg Gly Lys Val
145                 150                 155                 160

CGT TTC CTG ATG CTT GTA GGA GGG TCC ACC CTC TGC GTC AGG CGG GCC      528
Arg Phe Leu Met Leu Val Gly Gly Ser Thr Leu Cys Val Arg Arg Ala
                165                 170                 175

CCA CCC ACC ACA GCT GTC CCC AGC AGA ACC TCT CTA GTC CTC ACA CTG      576
Pro Pro Thr Thr Ala Val Pro Ser Arg Thr Ser Leu Val Leu Thr Leu
            180                 185                 190

AAC GAG CTC CCA AAC AGG ACT TCT GGA TTG TTG GAG ACA AAC TTC ACT      624
Asn Glu Leu Pro Asn Arg Thr Ser Gly Leu Leu Glu Thr Asn Phe Thr
        195                 200                 205

GCC TCA GCC AGA ACT ACT GGC TCT GGG CTT CTG AAG TGG CAG CAG GGA      672
Ala Ser Ala Arg Thr Thr Gly Ser Gly Leu Leu Lys Trp Gln Gln Gly
    210                 215                 220

TTC AGA GCC AAG ATT CCT GGT CTG CTG AAC CAA ACC TCC AGG TCC CTG      720
Phe Arg Ala Lys Ile Pro Gly Leu Leu Asn Gln Thr Ser Arg Ser Leu
225                 230                 235                 240

GAC CAA ATC CCC GGA TAC CTG AAC AGG ATA CAC GAA CTC TTG AAT GGA      768
Asp Gln Ile Pro Gly Tyr Leu Asn Arg Ile His Glu Leu Leu Asn Gly
                245                 250                 255
```

```
ACT CGT GGA CTC TTT CCT GGA CCC TCA CGC AGG ACC CTA GGA GCC CCG        816
Thr Arg Gly Leu Phe Pro Gly Pro Ser Arg Arg Thr Leu Gly Ala Pro
        260                 265                 270

GAC ATT TCC TCA GGA ACA TCA GAC ACA GGC TCC CTG CCA CCC AAC CTC        864
Asp Ile Ser Ser Gly Thr Ser Asp Thr Gly Ser Leu Pro Pro Asn Leu
            275                 280                 285

CAG CCT GGA TAT TCT CCT TCC CCA ACC CAT CCT CCT ACT GGA CAG TAT        912
Gln Pro Gly Tyr Ser Pro Ser Pro Thr His Pro Pro Thr Gly Gln Tyr
290                 295                 300

ACG CTC TTC CCT CTT CCA CCC ACC TTG CCC ACC CCT GTG GTC CAG CTC        960
Thr Leu Phe Pro Leu Pro Pro Thr Leu Pro Thr Pro Val Val Gln Leu
305                 310                 315                 320

CAC CCC CTG CTT CCT GAC CCT TCT GCT CCA ACG CCC ACC CCT ACC AGC       1008
His Pro Leu Leu Pro Asp Pro Ser Ala Pro Thr Pro Thr Pro Thr Ser
                325                 330                 335

CCT CTT CTA AAC ACA TCC TAC ACC CAC TCC CAG AAT CTG TCT CAG GAA       1056
Pro Leu Leu Asn Thr Ser Tyr Thr His Ser Gln Asn Leu Ser Gln Glu
                340                 345                 350

GGG TAA                                                                1062
Gly
```

(2) INFORMATION FOR SEQ ID NO:4:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Leu Thr Glu Leu Leu Val Val Met Leu Leu Thr Ala
1               5                   10                  15

Arg Leu Thr Leu Ser Ser Pro Ala Pro Ala Cys Asp Leu Arg Val
                20                  25                  30

Leu Ser Lys Leu Leu Arg Asp Ser His Val Leu His Ser Arg Leu Ser
            35                  40                  45

Gln Cys Pro Glu Val His Pro Leu Pro Thr Pro Val Leu Leu Pro Ala
    50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
    130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
            180                 185                 190

Asn Glu Leu Pro Asn Arg Thr Ser Gly Leu Leu Glu Thr Asn Phe Thr
        195                 200                 205

Ala Ser Ala Arg Thr Thr Gly Ser Gly Leu Leu Lys Trp Gln Gln Gly
```

|  |  |  | 210 |  |  |  | 215 |  |  |  | 220 |  |  |
|---|---|---|---|---|---|---|---|---|---|---|---|---|---|

```
Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
            260                 265                 270

Asp Ile Ser Ser Gly Thr Ser Asp Thr Gly Ser Leu Pro Pro Asn Leu
            275                 280                 285

Gln Pro Gly Tyr Ser Pro Ser Pro Thr His Pro Thr Gly Gln Tyr
        290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
                325                 330                 335

Pro Leu Leu Asn Thr Ser Tyr Thr His Ser Gln Asn Leu Ser Gln Glu
                340                 345                 350

Gly
```

(2) INFORMATION FOR SEQ ID NO:5:

(i) SEQUENCE CHARACTERISTICS:
        (A) LENGTH: 4823 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(632..644, 876..1003, 1290..1376,
            3309..3476, 3713..4375)

(xi) SEQUENCE DESCRIPTION: SEQ ID NO:5:

```
CTTTCTTGCT TTCTTTCTTT CTTTCTTTCT TTCTTTTTTT TTTTTGAGAC GGAGTTTCAC      60

TCTTATTGCC CAGGCTGGAG TGCAATGGTG CGATCTCGGC TCACCACAAC CTCCGCCTCC     120

CAGGTACAAG CGATTCTCCT GTCTCAGCCT CCCAAGTAGC TTGGATTACA GGCATGAACC     180

ACCACACCCT GCTAGTTTTT TTGTATTTCG TAGAGCCGGG GTTTCACCAT GTTAGTGAGG     240

CTGGTGGCGA ACTCCTGACC TCAGGTGATC CACCCGCCTT GGACTCCCAA AGTGCTGGGA     300

TTACAGGCAT GAGCCACTGC ACCCGGCACA CCATATGCTT TCATCACAAG AAAATGTGAG     360

AGAATTCAGG GCTTTGGCAG TTCCAGGCTG GTCAGCATCT CAAGCCCTCC CCAGCATCTG     420

TTCACCCTGC CAGGCAGTCT CTTCCTAGAA ACTTGGTTAA ATGTTCACTC TTCTTGCTAC     480

TTTCAGGATA GATTCTTCAC CCTTGGTCCG CCTTTGCCCC ACCCTACTCT GCCCAGAAGT     540

GCAAGAGCCT AAGCCGCCTC CATGGCCCCA GGAAGGATTC AGGGGAGAGG CCCCAAACAG     600

GGAGCCACGC CAGCCAGACA CCCCGGCCAG A ATG GAG CTG ACT  G GTGAGAACAC      654
                                 Met Glu Leu Thr
                                  1

ACCTGAGGGG CTAGGGCCAT ATGGAAACAT GACAGAAGGG GAGAGAGAAA GGAGACACGC     714

TGCAGGGGGC AGGAAGCTGG GGGAACCCAT TCTCCCAAAA ATAAGGGGTC TGAGGGGTGG     774

ATTCCCTGGG TTTCAGGTCT GGGTCCTGAA TGGGAATTCC TGGAATACCA GCTGACAATG     834

ATTTCCTCCT CATCTTTCAA CCTCACCTCT CCTCATCTAA G  AA TTG CTC CTC         886
                                              Glu Leu Leu Leu
                                                   5
```

| | |
|---|---|
| GTG GTC ATG CTT CTC CTA ACT GCA AGG CTA ACG CTG TCC AGC CCG GCT<br>Val Val Met Leu Leu Leu Thr Ala Arg Leu Thr Leu Ser Ser Pro Ala<br>    10                    15                        20 | 934 |
| CCT CCT GCT TGT GAC CTC CGA GTC CTC AGT AAA CTG CTT CGT GAC TCC<br>Pro Pro Ala Cys Asp Leu Arg Val Leu Ser Lys Leu Leu Arg Asp Ser<br>25                    30                    35                    40 | 982 |
| CAT GTC CTT CAC AGC AGA CTG GTGAGAACTC CCAACATTAT CCCCTTTATC<br>His Val Leu His Ser Arg Leu<br>                45 | 1033 |
| CGCGTAACTG GTAAGACACC CATACTCCCA GGAAGACACC ATCACTTCCT CTAACTCCTT | 1093 |
| GACCCAATGA CTATTCTTCC CATATTGTCC CCACCTACTG ATCACACTCT CTGACAAGGA | 1153 |
| TTATTCTTCA CAATACAGCC CGCATTTAAA AGCTCTCGTC TAGAGATAGT ACTCATGGAG | 1213 |
| GACTAGCCTG CTTATTAGGC TACCATAGCT CTCTCTATTT CAGCTCCCTT CTCCCCCCAC | 1273 |
| CAATCTTTTT CAACAG AGC CAG TGC CCA GAG GTT CAC CCT TTG CCT ACA<br>                          Ser Gln Cys Pro Glu Val His Pro Leu Pro Thr<br>                                        50                    55 | 1322 |
| CCT GTC CTG CTG CCT GCT GTG GAC TTT AGC TTG GGA GAA TGG AAA ACC<br>Pro Val Leu Leu Pro Ala Val Asp Phe Ser Leu Gly Glu Trp Lys Thr<br>    60                    65                    70 | 1370 |
| CAG ATG GTAAGAAAGC CATCCCTAAC CTTGGCTTCC CTAAGTCCTG TCTTCAGTTT<br>Gln Met<br>75 | 1426 |
| CCCACTGCTT CCCATGGATT CTCCAACATT CTTGAGCTTT TTAAAAATAT CTCACCTTCA | 1486 |
| GCTTGGCCAC CCTAACCCAA TCTACATTCA CCTATGATGA TAGCCTGTGG ATAAGATGAT | 1546 |
| GGCTTGCAGG TCCAATATGT GAATAGATTT GAAGCTGAAC ACCATGAAAA GCTGGAGAGA | 1606 |
| AATCGCTCAT GGCCATGCCT TTGACCTATT CCCGTTCAGT CTTCTTAAAT TGGCATGAAG | 1666 |
| AAGCAAGACT CATATGTCAT CCACAGATGA CACAAAGCTG GGAAGTACCA CTAAAATAAC | 1726 |
| AAAAGACTGA ATCAAGATTC AAATCACTGA AAGACTAGGT CAAAAACAAG GTGAAACAAC | 1786 |
| AGAGATATAA ACTTCTACAT GTGGGCCGGG GGCTCACGCC TGTAATCCCA GCACTTTGGG | 1846 |
| AGGCCGAGGC AGGCAGATCA CCTGAGGGCA GGAGTTTGAG AGCAGCCTGG CCAACATGGC | 1906 |
| GAAACCCCGT CTCTACTAAG AATACAGAAT TAGCCGGGCA TGGTAGTGCA TGCCTGTAAT | 1966 |
| CCCAGCTACT TGGAAGGCTG AAGCAGGAGA ATCCCTTGAA CCCAGGAGGT GGAGGTTGTA | 2026 |
| GTGAGCTGAG ATCATGCCAA TGCACTCCAG CCTGGGTGAC AAGAGCAAAA CTCCGTCTCA | 2086 |
| AAAAGAAAAA AAAATTCTAC ATGTGTAAAT TAATGAGTAA AGTCCTATTC CAGCTTTCAG | 2146 |
| GCCACAATGC CCTGCTTCCA TCATTTAAGC CTCTGGCCCT AGCACTTCCT ACGAAAAGGA | 2206 |
| TCTGAGAGAA TTAAATTGCC CCCAAACTTA CCATGTAACA TTACTGAAGC TGCTATTCTT | 2266 |
| AAAGCTAGTA ATTCTTGTCT GTTTGATGTT TAGCATCCCC ATTGTGGAAA TGCTCGTACA | 2326 |
| GAACTCTATT CCGAGTGGAC TACACTTAAA TATACTGGCC TGAACACCGG ACATCCCCCT | 2386 |
| GAAGACATAT GCTAATTTAT TAAGAGGGAC CATATTAAAC TAACATGTGT CTAGAAAGCA | 2446 |
| GCAGCCTGAA CAGAAAGAGA CTAGAAGCAT GTTTTATGGG CAATAGTTTA AAAAACTAAA | 2506 |
| ATCTATCCTC AAGAACCCTA GCGTCCCTTC TTCCTTCAGG ACTGAGTCAG GGAAGAAGGG | 2566 |
| CAGTTCCTAT GGGTCCCTTC TAGTCCTTTC TTTTCATCCT TATGATCATT ATGGTAGAGT | 2626 |
| CTCATACCTA CATTTAGTTT ATTTATTATT ATTATTTGAG ACGGAGTCTC ACTCTATCCC | 2686 |
| CCAGGCTGGA GTGCAGTGGC ATGATCTCAA CTCACTGCAA CCTCAGCCTC CCGGATTCAA | 2746 |
| GCGATTCTCC TGTCTCAGTC TCCCAAGTAG CTGGGATTAC AGGTGCCCAC CACCATGCCC | 2806 |
| AGCTAATTTG TGTATTTGTG GTAGAGATGG GGTTTCACCA TGTTGGGCAG GCTGATCTTG | 2866 |

```
                                            -continued

AACTCCTGAC CTCAGGTGAT CCACCTGCCT CAGCCTCCCA AAGTGCTGGG ATTACAGGCG    2926

TGAGCCACTG CACCCAGCCT TCATTCAGTT TAAAAATCAA ATGATCCTAA GGTTTTGCAG    2986

CAGAAAGAGT AAATTTGCAG CACTAGAACC AAGAGGTAAA AGCTGTAACA GGGCAGATTT    3046

CAGCAACGTA AGAAAAAAGG AGCTCTTCTC ACTGAAACCA AGTGTAAGAC CAGGCTGGAC    3106

TAGAGGACAC GGGAGTTTTT GAAGCAGAGG CTGATGACCA GCTGTCGGGA GACTGTGAAG    3166

GAATTCCTGC CCTGGGTGGG ACCTTGGTCC TGTCCAGTTC TCAGCCTGTA TGATTCACTC    3226

TGCTGGCTAC TCCTAAGGCT CCCCACCCGC TTTTAGTGTG CCCTTTGAGG CAGTGCGCTT    3286

CTCTCTTCCA TCTCTTTCTC AG GAG GAG ACC AAG GCA CAG GAC ATT CTG GGA    3338
                         Glu Glu Thr Lys Ala Gln Asp Ile Leu Gly
                                      80                  85

GCA GTG ACC CTT CTG CTG GAG GGA GTG ATG GCA GCA CGG GGA CAA CTG     3386
Ala Val Thr Leu Leu Leu Glu Gly Val Met Ala Ala Arg Gly Gln Leu
             90                  95                 100

GGA CCC ACT TGC CTC TCA TCC CTC CTG GGG CAG CTT TCT GGA CAG GTC     3434
Gly Pro Thr Cys Leu Ser Ser Leu Leu Gly Gln Leu Ser Gly Gln Val
        105                 110                 115

CGT CTC CTC CTT GGG GCC CTG CAG AGC CTC CTT GGA ACC CAG                 3476
Arg Leu Leu Leu Gly Ala Leu Gln Ser Leu Leu Gly Thr Gln
    120                 125                 130

GTAAGTCCCC AGTCAAGGGA TCTGTAGAAA CTGTTCTTTT CTGACTCAGT CCCCCTAGAA    3536

GACCTGAGGG AAGAAGGGCT CTTCCAGGGA GCTCAAGGGC AGAAGAGCTG ATCTACTAAG    3596

AGTGCTCCCT GCCAGCCACA ATGCCTGGGT ACTGGCATCC TGTCTTTCCT ACTTAGACAA    3656

GGGAGGCCTG AGATCTGGCC CTGGTGTTTG GCCTCAGGAC CATCCTCTGC CCTCAG         3712

CTT CCT CCA CAG GGC AGG ACC ACA GCT CAC AAG GAT CCC AAT GCC ATC     3760
Leu Pro Pro Gln Gly Arg Thr Thr Ala His Lys Asp Pro Asn Ala Ile
            135                 140                 145

TTC CTG AGC TTC CAA CAC CTG CTC CGA GGA AAG GTG CGT TTC CTG ATG     3808
Phe Leu Ser Phe Gln His Leu Leu Arg Gly Lys Val Arg Phe Leu Met
        150                 155                 160

CTT GTA GGA GGG TCC ACC CTC TGC GTC AGG CGG GCC CCA CCC ACC ACA     3856
Leu Val Gly Gly Ser Thr Leu Cys Val Arg Arg Ala Pro Pro Thr Thr
165                 170                 175                 180

GCT GTC CCC AGC AGA ACC TCT CTA GTC CTC ACA CTG AAC GAG CTC CCA     3904
Ala Val Pro Ser Arg Thr Ser Leu Val Leu Thr Leu Asn Glu Leu Pro
                185                 190                 195

AAC AGG ACT TCT GGA TTG TTG GAG ACA AAC TTC ACT GCC TCA GCC AGA     3952
Asn Arg Thr Ser Gly Leu Leu Glu Thr Asn Phe Thr Ala Ser Ala Arg
            200                 205                 210

ACT ACT GGC TCT GGG CTT CTG AAG TGG CAG CAG GGA TTC AGA GCC AAG     4000
Thr Thr Gly Ser Gly Leu Leu Lys Trp Gln Gln Gly Phe Arg Ala Lys
        215                 220                 225

ATT CCT GGT CTG CTG AAC CAA ACC TCC AGG TCC CTG GAC CAA ATC CCC     4048
Ile Pro Gly Leu Leu Asn Gln Thr Ser Arg Ser Leu Asp Gln Ile Pro
230                 235                 240

GGA TAC CTG AAC AGG ATA CAC GAA CTC TTG AAT GGA ACT CGT GGA CTC     4096
Gly Tyr Leu Asn Arg Ile His Glu Leu Leu Asn Gly Thr Arg Gly Leu
245                 250                 255                 260

TTT CCT GGA CCC TCA CGC AGG ACC CTA GGA GCC CCG GAC ATT TCC TCA     4144
Phe Pro Gly Pro Ser Arg Arg Thr Leu Gly Ala Pro Asp Ile Ser Ser
                265                 270                 275

GGA ACA TCA GAC ACA GGC TCC CTG CCA CCC AAC CTC CAG CCT GGA TAT     4192
Gly Thr Ser Asp Thr Gly Ser Leu Pro Pro Asn Leu Gln Pro Gly Tyr
            280                 285                 290

TCT CCT TCC CCA ACC CAT CCT CCT ACT GGA CAG TAT ACG CTC TTC CCT     4240
Ser Pro Ser Pro Thr His Pro Pro Thr Gly Gln Tyr Thr Leu Phe Pro
```

```
                 295                 300                 305
CTT CCA CCC ACC TTG CCC ACC CCT GTG GTC CAG CTC CAC CCC CTG CTT      4288
Leu Pro Pro Thr Leu Pro Thr Pro Val Val Gln Leu His Pro Leu Leu
    310                 315                 320

CCT GAC CCT TCT GCT CCA ACG CCC ACC CCT ACC AGC CCT CTT CTA AAC      4336
Pro Asp Pro Ser Ala Pro Thr Pro Thr Pro Thr Ser Pro Leu Leu Asn
325                 330                 335                 340

ACA TCC TAC ACC CAC TCC CAG AAT CTG TCT CAG GAA GGG TAAGGTTCTC       4385
Thr Ser Tyr Thr His Ser Gln Asn Leu Ser Gln Glu Gly
                345                 350

AGACACTGCC GACATCAGCA TTGTCTCGTG TACAGCTCCC TTCCCTGCAG GGCGCCCCTG    4445

GGAGACAACT GGACAAGATT TCCTACTTTC TCCTGAAACC CAAAGCCCTG GTAAAAGGGA    4505

TACACAGGAC TGAAAAGGGA ATCATTTTTC ACTGTACATT ATAAACCTTC AGAAGCTATT    4565

TTTTTAAGCT ATCAGCAATA CTCATCAGAG CAGCTAGCTC TTTGGTCTAT TTTCTGCAGA    4625

AATTTGCAAC TCACTGATTC TCAACATGCT CTTTTTCTGT GATAACTCTG CAAAGACCTG    4685

GGCTGGCCTG GCAGTTGAAC AGAGGGAGAG ACTAACCTTG AGTCAGAAAA CAGAGGAAGG    4745

GTAATTTCCT TTGCTTCAAA TTCAAGGCCT TCCAACGCCC CCATCCCCTT TACTATCATT    4805

CTCAGTGGGA CTCTGATC                                                  4823

(2) INFORMATION FOR SEQ ID NO:6:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Leu Thr Glu Leu Leu Val Val Met Leu Leu Thr Ala
1               5                   10                  15

Arg Leu Thr Leu Ser Ser Pro Ala Pro Ala Cys Asp Leu Arg Val
            20                  25                  30

Leu Ser Lys Leu Leu Arg Asp Ser His Val Leu His Ser Arg Leu Ser
        35                  40                  45

Gln Cys Pro Glu Val His Pro Leu Pro Thr Pro Val Leu Leu Pro Ala
50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
    130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
            180                 185                 190

Asn Glu Leu Pro Asn Arg Thr Ser Gly Leu Leu Glu Thr Asn Phe Thr
        195                 200                 205
```

Ala Ser Ala Arg Thr Thr Gly Ser Gly Leu Leu Lys Trp Gln Gln Gly
    210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
            260                 265                 270

Asp Ile Ser Ser Gly Thr Ser Asp Thr Gly Ser Leu Pro Pro Asn Leu
        275                 280                 285

Gln Pro Gly Tyr Ser Pro Ser Pro Thr His Pro Pro Thr Gly Gln Tyr
    290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
                325                 330                 335

Pro Leu Leu Asn Thr Ser Tyr Thr His Ser Gln Asn Leu Ser Gln Glu
            340                 345                 350

Gly (2) INFORMATION FOR SEQ ID NO:7:

(i) SEQUENCE CHARACTERISTICS:
        (A) LENGTH: 633 amino acids
        (B) TYPE: amino acid
        (D) TOPOLOGY: linear (ii) MOLECULE TYPE: protein (xi) SEQUENCE DESCRIPTION: SEQ ID NO:7:

Met Pro Ser Trp Ala Leu Phe Met Val Thr Ser Cys Leu Leu Leu Ala
1               5                   10                  15

Leu Pro Asn Gln Ala Gln Val Thr Ser Gln Asp Val Phe Leu Leu Ala
                20                  25                  30

Leu Gly Thr Glu Pro Leu Asn Cys Phe Ser Gln Thr Phe Glu Asp Leu
            35                  40                  45

Thr Cys Phe Trp Asp Glu Glu Ala Ala Pro Ser Gly Thr Tyr Gln
50                  55                  60

Leu Leu Tyr Ala Tyr Arg Gly Glu Lys Pro Arg Ala Cys Pro Leu Tyr
65              70                  75                  80

Ser Gln Ser Val Pro Thr Phe Gly Thr Arg Tyr Val Cys Gln Phe Pro
                85                  90                  95

Ala Gln Asp Glu Val Arg Leu Phe Phe Pro Leu His Leu Trp Val Lys
            100                 105                 110

Asn Val Ser Leu Asn Gln Thr Leu Ile Gln Arg Val Leu Phe Val Asp
        115                 120                 125

Ser Val Gly Leu Pro Ala Pro Pro Arg Val Ile Lys Ala Arg Gly Gly
    130                 135                 140

Ser Gln Pro Gly Glu Leu Gln Ile His Trp Glu Ala Pro Ala Pro Glu
145                 150                 155                 160

Ile Ser Asp Phe Leu Arg His Glu Leu Arg Tyr Gly Pro Thr Asp Ser
                165                 170                 175

Ser Asn Ala Thr Ala Pro Ser Val Ile Gln Leu Leu Ser Thr Glu Thr
            180                 185                 190

Cys Cys Pro Thr Leu Trp Met Pro Asn Pro Val Pro Val Leu Asp Gln
        195                 200                 205

-continued

```
Pro Pro Cys Val His Pro Thr Ala Ser Gln Pro His Gly Pro Val Arg
    210                 215                 220

Thr Ser Pro Ala Gly Glu Ala Pro Phe Leu Thr Val Lys Gly Gly Ser
225                 230                 235                 240

Cys Leu Val Ser Gly Leu Gln Ala Gly Lys Ser Tyr Trp Leu Gln Leu
                245                 250                 255

Arg Ser Gln Pro Asp Gly Val Ser Leu Arg Gly Ser Trp Gly Pro Trp
            260                 265                 270

Ser Phe Pro Val Thr Val Asp Leu Pro Gly Asp Ala Val Thr Ile Gly
        275                 280                 285

Leu Gln Cys Phe Thr Leu Asp Leu Lys Met Val Thr Cys Gln Trp Gln
    290                 295                 300

Gln Gln Asp Arg Thr Ser Ser Gln Gly Phe Phe Arg His Ser Arg Thr
305                 310                 315                 320

Arg Cys Cys Pro Thr Asp Arg Asp Pro Thr Trp Glu Lys Cys Glu Glu
                325                 330                 335

Glu Glu Pro Arg Pro Gly Ser Gln Pro Ala Leu Val Ser Arg Cys His
            340                 345                 350

Phe Lys Ser Arg Asn Asp Ser Val Ile His Ile Leu Val Glu Val Thr
        355                 360                 365

Thr Ala Gln Gly Ala Val His Ser Tyr Leu Gly Ser Pro Phe Trp Ile
    370                 375                 380

His Gln Ala Val Leu Leu Pro Thr Pro Ser Leu His Trp Arg Glu Val
385                 390                 395                 400

Ser Ser Gly Arg Leu Glu Leu Glu Trp Gln His Gln Ser Ser Trp Ala
                405                 410                 415

Ala Gln Glu Thr Cys Tyr Gln Leu Arg Tyr Thr Gly Glu Gly Arg Glu
            420                 425                 430

Asp Trp Lys Val Leu Glu Pro Ser Leu Gly Ala Arg Gly Gly Thr Leu
        435                 440                 445

Glu Leu Arg Pro Arg Ala Arg Tyr Ser Leu Gln Leu Arg Ala Arg Leu
    450                 455                 460

Asn Gly Pro Thr Tyr Gln Gly Pro Trp Ser Ala Trp Ser Pro Pro Ala
465                 470                 475                 480

Arg Val Ser Thr Gly Ser Glu Thr Ala Trp Ile Thr Leu Val Thr Ala
                485                 490                 495

Leu Leu Leu Val Leu Ser Leu Ser Ala Leu Leu Gly Leu Leu Leu Leu
            500                 505                 510

Lys Trp Gln Phe Pro Ala His Tyr Arg Arg Leu Arg His Ala Leu Trp
        515                 520                 525

Pro Ser Leu Pro Asp Leu His Arg Val Leu Gly Gln Tyr Leu Arg Asp
    530                 535                 540

Thr Ala Ala Leu Ser Pro Ser Lys Ala Thr Val Thr Asp Ser Cys Glu
545                 550                 555                 560

Glu Val Glu Pro Ser Leu Leu Glu Ile Leu Pro Lys Ser Ser Glu Ser
                565                 570                 575

Thr Pro Leu Pro Leu Cys Pro Ser Gln Pro Gln Met Asp Tyr Arg Gly
            580                 585                 590

Leu Gln Pro Cys Leu Arg Thr Met Pro Leu Ser Val Cys Pro Pro Met
        595                 600                 605

Ala Glu Thr Gly Ser Cys Cys Thr Thr His Ile Ala Asn His Ser Tyr
    610                 615                 620

Leu Pro Leu Ser Tyr Trp Gln Gln Pro
```

625          630

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: ZC7422

(xi) SEQUENCE DESCRIPTION: SEQ ID NO:8:

GGAAGCTGGG TACCAAGGAG GCT                                                 23

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: ZC7423

(xi) SEQUENCE DESCRIPTION: SEQ ID NO:9:

AGCCTCCTTG GTACCCAGCT TCC                                                 23

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (vii) IMMEDIATE SOURCE:
        (B) CLONE: ZC7424

(xi) SEQUENCE DESCRIPTION: SEQ ID NO:10:

TTAGACACCT GGCCAGAATG                                                        20

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (vii) IMMEDIATE SOURCE:
        (B) CLONE: ZC7421

(xi) SEQUENCE DESCRIPTION: SEQ ID NO:11:

TGATGTCGGC AGTGTCTGAG AACC                                              24

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (vii) IMMEDIATE SOURCE:
        (B) CLONE: ZC7454

(xi) SEQUENCE DESCRIPTION: SEQ ID NO:12:

```
CCGGAATTCT TAGACACCTG GCCAGAATG                                              29

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (vii) IMMEDIATE SOURCE:
        (B) CLONE: ZC7453

(xi) SEQUENCE DESCRIPTION: SEQ ID NO:13:

CCGGAATTCT GATGTCGGCA GTGTCTGAGA ACC                                         33

(2) INFORMATION FOR SEQ ID NO:14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (vii) IMMEDIATE SOURCE:
        (B) CLONE: ZC5499

(xi) SEQUENCE DESCRIPTION: SEQ ID NO:14:

CGAGCCACTT TCTGCACTCC TCGAGTTTTT TTTTTTTTTT TT                               42

(2) INFORMATION FOR SEQ ID NO:15:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (vii) IMMEDIATE SOURCE:
        (B) CLONE: ZC5746

(xi) SEQUENCE DESCRIPTION: SEQ ID NO:15:

GAGAGAGAGA GAGAATTCAT GCCCTCCTGG GCCCTCTTCA TGGTC                            45

(2) INFORMATION FOR SEQ ID NO:16:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (vii) IMMEDIATE SOURCE:
        (B) CLONE: ZC5762

(xi) SEQUENCE DESCRIPTION: SEQ ID NO:16:

AGAGAGAGAG AGAGCTCGAG TCAAGGCTGC TGCCAATAGC TTAGTGGTAG GT                    52

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (vii) IMMEDIATE SOURCE:
        (B) CLONE: ZC5742

(xi) SEQUENCE DESCRIPTION: SEQ ID NO:17:
```

```
GACCCTGGAG CTGCGCCCGC GATCTCGCTA                                              30

(2) INFORMATION FOR SEQ ID NO:18:

(i) SEQUENCE CHARACTERISTICS:
          (A) LENGTH: 49 base pairs
          (B) TYPE: nucleic acid
          (C) STRANDEDNESS: single
          (D) TOPOLOGY: linear (vii) IMMEDIATE SOURCE:
          (B) CLONE: ZC6091

(xi) SEQUENCE DESCRIPTION: SEQ ID NO:18:

GAGCACAGAA TTCACTACTC GAGGCGGCCG CTTTTTTTTT TTTTTTTTT                          49

(2) INFORMATION FOR SEQ ID NO:19:

(i) SEQUENCE CHARACTERISTICS:
          (A) LENGTH: 8 amino acids
          (B) TYPE: amino acid
          (D) TOPOLOGY: linear (xi) SEQUENCE DESCRIPTION: SEQ ID NO:19:

Val Arg Thr Ser Pro Ala Gly Glu
1               5

(2) INFORMATION FOR SEQ ID NO:20:

(i) SEQUENCE CHARACTERISTICS:
          (A) LENGTH: 45 base pairs
          (B) TYPE: nucleic acid
          (C) STRANDEDNESS: single
          (D) TOPOLOGY: linear (vii) IMMEDIATE SOURCE:
          (B) CLONE: ZC6603

(xi) SEQUENCE DESCRIPTION: SEQ ID NO:20:

GAGGAATTCG CAGAAGCCAT GCCCTCTTGG GCCCTCTTCA TGGTC                              45

(2) INFORMATION FOR SEQ ID NO:21:

(i) SEQUENCE CHARACTERISTICS:
          (A) LENGTH: 48 base pairs
          (B) TYPE: nucleic acid
          (C) STRANDEDNESS: single
          (D) TOPOLOGY: linear (vii) IMMEDIATE SOURCE:
          (B) CLONE: ZC6704

(xi) SEQUENCE DESCRIPTION: SEQ ID NO:21:

GAAGAGGAAT TCACCATGGA TGTCTTCTTG CTGGCCTTGG GCACAGAG                           48

(2) INFORMATION FOR SEQ ID NO:22:

(i) SEQUENCE CHARACTERISTICS:
          (A) LENGTH: 60 base pairs
          (B) TYPE: nucleic acid
          (C) STRANDEDNESS: single
          (D) TOPOLOGY: linear (vii) IMMEDIATE SOURCE:
          (B) CLONE: ZC6703

(xi) SEQUENCE DESCRIPTION: SEQ ID NO:22:

CGACTTTACC TCGAGTGCTA CTGATGCTCT TCTGCCAGCA GTCTCGGAGC CGTGGACAC              60
```

-continued (2) INFORMATION FOR SEQ ID NO:23:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (vii) IMMEDIATE SOURCE:
      (B) CLONE: ZC6707

(xi) SEQUENCE DESCRIPTION: SEQ ID NO:23:

AATTCGCCAT GGGACTCGAG CATCACCATC ACCATCACTG AG                42

(2) INFORMATION FOR SEQ ID NO:24:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (vii) IMMEDIATE SOURCE:
      (B) CLONE: ZC6706

(xi) SEQUENCE DESCRIPTION: SEQ ID NO:24:

GATCCTCAGT GATGGTGATG GTGATGCTCG AGTCCCATGG CG                42